United States Patent
Dooley et al.

(10) Patent No.: US 11,921,116 B2
(45) Date of Patent: Mar. 5, 2024

(54) ENIGMA AND CDH18 AS COMPANION DIAGNOSTICS FOR CDK4 INHIBITORS

(71) Applicant: Memorial Sloan Kettering Cancer Center, New York, NY (US)

(72) Inventors: Mary Elizabeth Dooley, New York, NY (US); Marta Kovatcheva, New York, NY (US); Samuel Singer, New York, NY (US); William D. Tap, New York, NY (US); Aimee Crago, New York, NY (US); Andrew Koff, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 306 days.

(21) Appl. No.: 16/083,425

(22) PCT Filed: Mar. 9, 2017

(86) PCT No.: PCT/US2017/021560
§ 371 (c)(1),
(2) Date: Sep. 7, 2018

(87) PCT Pub. No.: WO2017/156263
PCT Pub. Date: Sep. 14, 2017

(65) Prior Publication Data
US 2019/0310259 A1    Oct. 10, 2019

Related U.S. Application Data

(60) Provisional application No. 62/306,000, filed on Mar. 9, 2016.

(51) Int. Cl.
*G01N 31/00* (2006.01)
*C12Q 1/6886* (2018.01)
*G01N 33/53* (2006.01)
*G01N 33/574* (2006.01)

(52) U.S. Cl.
CPC ..... *G01N 33/57488* (2013.01); *C12Q 1/6886* (2013.01); *G01N 33/574* (2013.01); *C12Q 2600/106* (2013.01); *C12Q 2600/158* (2013.01); *G01N 2333/70503* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,946,778 A | 8/1990 | Ladner et al. |
| 5,225,539 A | 7/1993 | Winter |
| 6,630,464 B1 | 10/2003 | Kelley et al. |
| 6,818,663 B2 | 11/2004 | Chu et al. |
| 9,889,135 B2 * | 2/2018 | Koff ............. G01N 33/57496 |
| 2002/0064779 A1 | 5/2002 | Landegren et al. |
| 2005/0003361 A1 | 1/2005 | Fredriksson |
| 2008/0293051 A1 | 11/2008 | Levy et al. |
| 2011/0152244 A1 | 6/2011 | Besong et al. |
| 2012/0207763 A1 | 8/2012 | Brain et al. |
| 2012/0244110 A1 | 9/2012 | Chen et al. |

FOREIGN PATENT DOCUMENTS

| | | | |
|---|---|---|---|
| EP | 0125023 B1 | 6/1991 | |
| EP | 0519596 A1 | 12/1992 | |
| EP | 0120694 B1 | 7/1993 | |
| EP | 0194276 B1 | 8/1993 | |
| EP | 0239400 B1 | 8/1994 | |
| EP | 0451216 B1 | 1/1996 | |
| WO | WO 1986/01533 | 3/1986 | |
| WO | WO-2013049680 A1 * | 4/2013 | ....... G01N 33/57492 |
| WO | WO 2014/172479 A1 | 10/2014 | |

OTHER PUBLICATIONS

Jung et al., "Enigma negatively regulates p53 through MDM2 and promotes tumor cell survival in mice," Journal of Clinical Investigation, vol. 120, No. 12, pp. 4496-4506 (Dec. 1, 2010) (Year: 2010).*

Jung et al., (Journal of Clinical Investigation, vol. 120, No. 12, pp. 4496-4506, Dec. 1, 2010). (Year: 2010).*

Jung et al., (Journal of Clinical Investigation, vol. 120, No. 12, pp. 4496-4506, Dec. 1, 2010—IDS filed Sep. 7, 2018) (Year: 2010).*

Jung et al., (Journal of Clinical Investigation, vol. 120, No. 12, pp. 4496-4506) (Year: 2010).*

Kovatcheva et al (Oncotarget, vol. 6, No. 10, pp. 8226-8243). (Year: 2015).*

International Search Report and Written Opinion, PCT/US2017/021560, Memorial Sloan Kettering Cancer Center, 12 pages (dated Jun. 16, 2017).

Jung et al., "Enigma negatively regulates p53 through MDM2 and promotes tumor cell survival in mice," Journal of Clinical Investigation, vol. 120, No. 12, pp. 4496-4506 (Dec. 1, 2010) DOI: 10.1172/JCI42674.

(Continued)

*Primary Examiner* — Lisa V Cook

(74) *Attorney, Agent, or Firm* — Foley & Lardner LLP

(57) ABSTRACT

The present disclosure relates to the use of one or more biomarkers to evaluate the likelihood that a CDK4 inhibitor would produce an anti-cancer effect in a subject. Accordingly, in certain non-limiting embodiments, the present disclosure provides for methods, compositions and kits for a companion diagnostic for CDK4 inhibitors, and in particular, for the use of the colocalization of Enigma and CDH18 biomarkers to foci within the cancer for determining whether the cancer can be successfully treated by CDK4 inhibition.

13 Claims, 21 Drawing Sheets
Specification includes a Sequence Listing.

(56) References Cited

OTHER PUBLICATIONS

Yadav et al., "The CDK4/6 inhibitor LY2835219 overcomes vemurafenib resistance resulting from MAPK reactivation and cyclin D1 upregulation," Molecular Cancer Therapeutics, vol. 13, No. 10, pp. 2253-2263 (Aug. 13, 2014).
Durick et al., Mol. and Cell. Bio. 18(4): 2298-2308 (1998).
Kuroda et al., J. Biol. Chem. 271:31029-31032 (1996).
Wu et al., J. Biol. Chem. 271 : 15934-15941 (1996).
Newman et al., BioTechnology, 10: 1455-1460 (1992).
Bird et al., Science, 242: 423-426 (1988).
Kovatcheva et al. Oncotarget, 6(10):8226-8243 (2015).

* cited by examiner

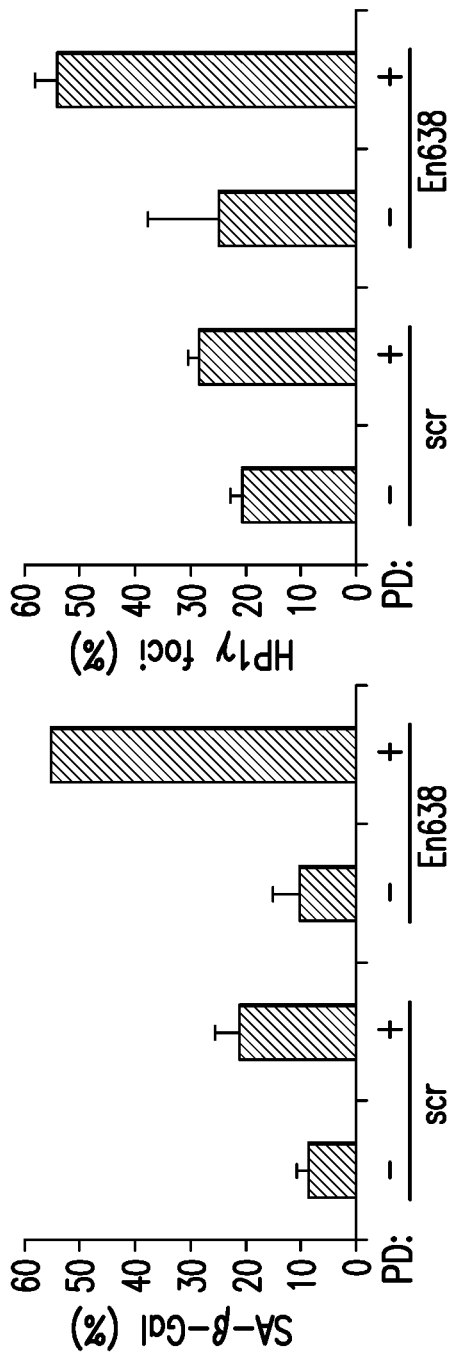
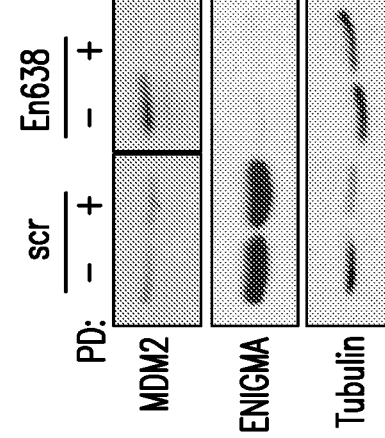
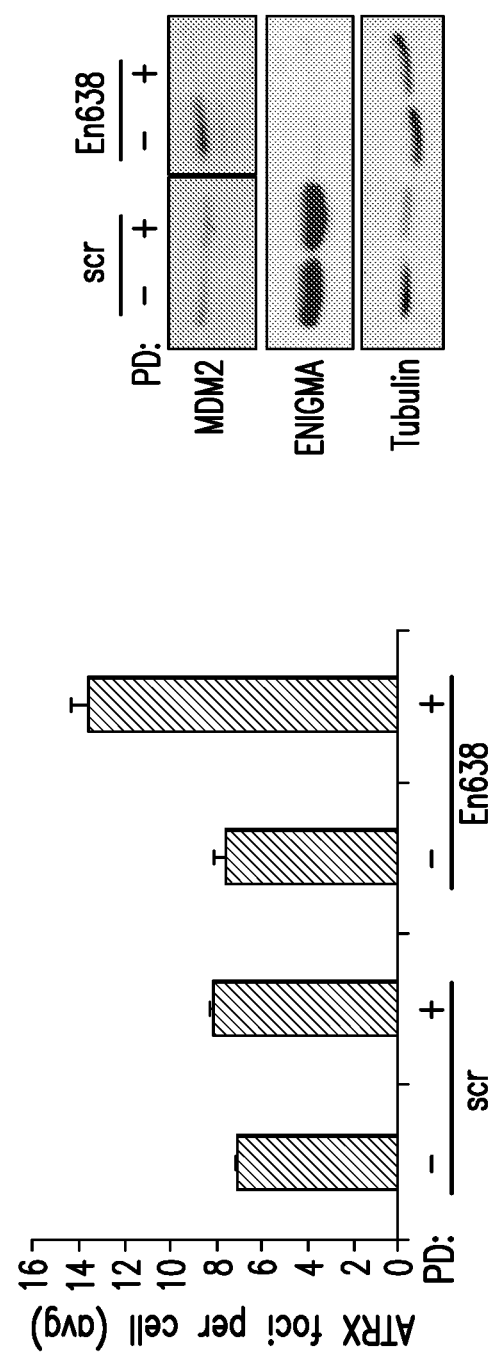
FIG. 3A  FIG. 3B  FIG. 3C  FIG. 3D

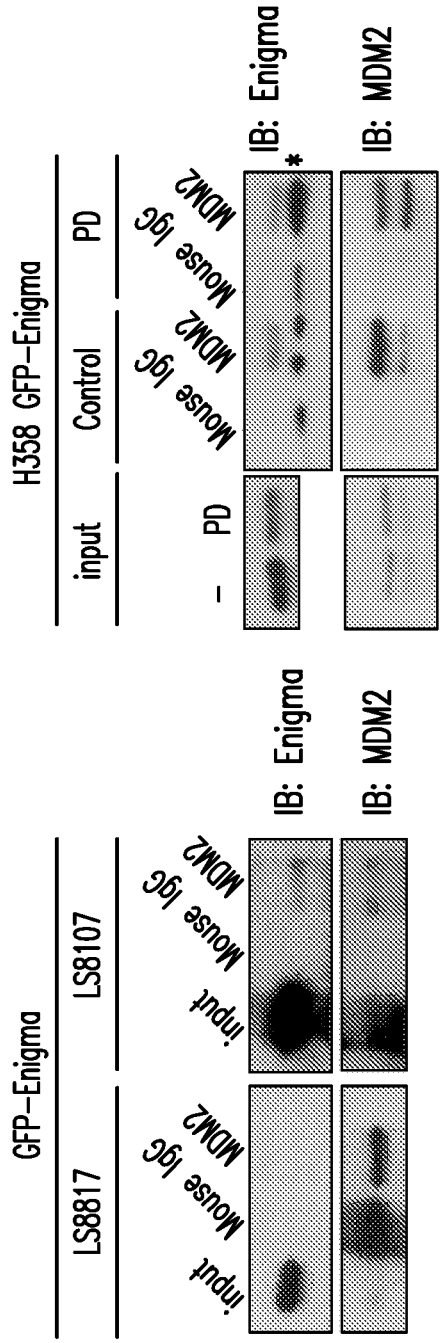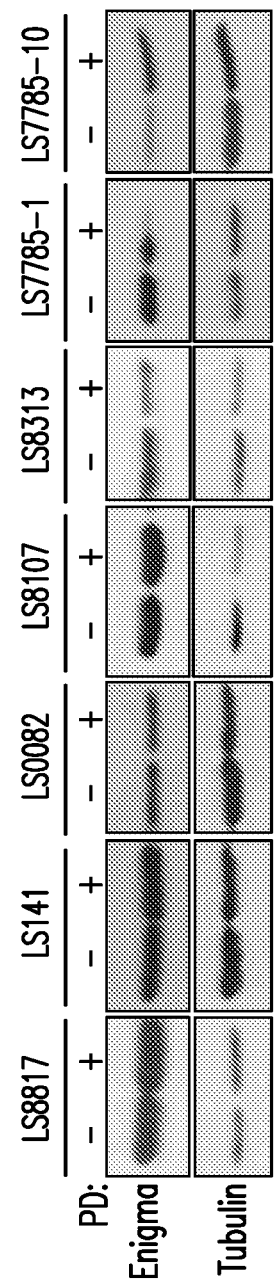
FIG. 7A
FIG. 7B
FIG. 7C

FIGURE 12
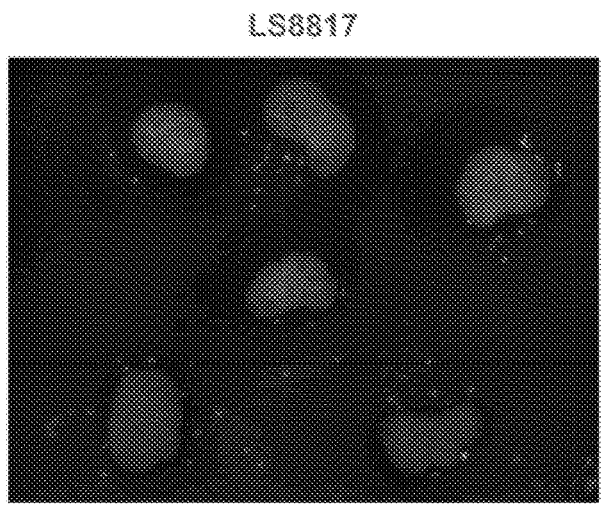 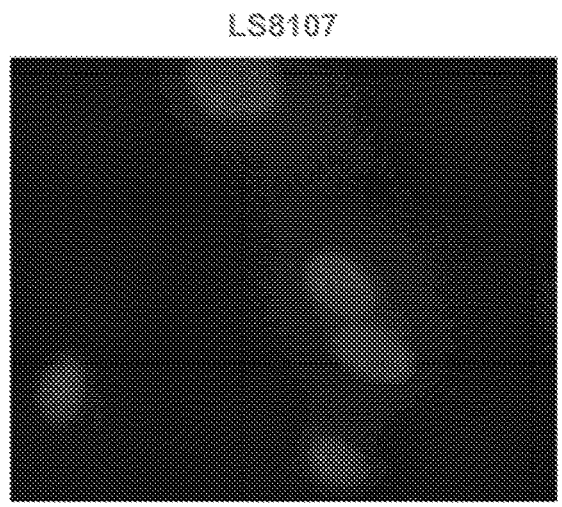

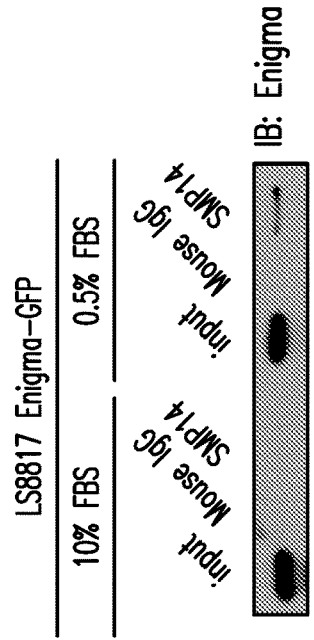
FIG. 13C
FIG. 13D
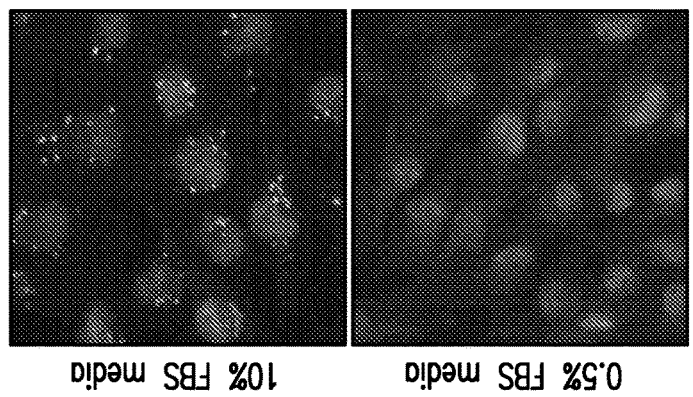
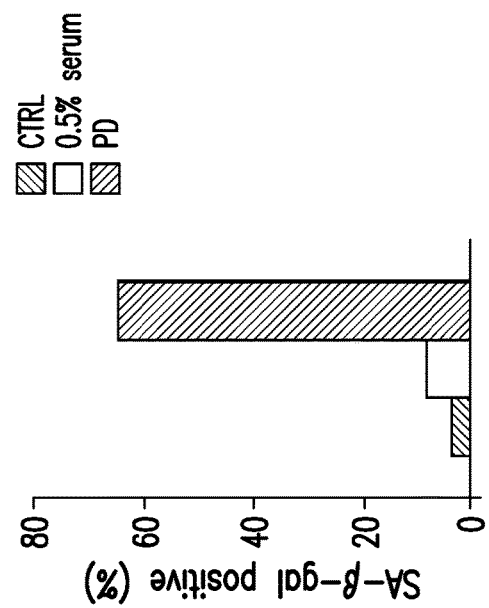
FIG. 13A
FIG. 13B

FIGURE 15A-B

|          | LS8817   | LS8107   | LS7785-10 | LS7785-1 | Type 1/2 | Tested |
|----------|----------|----------|-----------|----------|----------|--------|
| CDH12P1  | 0.50     | 0.50     | 0.50      | 0.50     |          |        |
| CDH12P2  | 0.50     | 2.38     | 4.15      | 0.50     |          |        |
| CDH12P3  | 0.50     | 0.50     | 0.50      | 0.50     |          |        |
| CDH12P4  | 0.50     | 0.50     | 0.50      | 0.50     |          |        |
| CDH17    | 0.50     | 1.34     | 0.50      | 4.32     |          |        |
| CDH19    | 0.50     | 1.34     | 0.50      | 0.50     |          |        |
| CDH20    | 0.50     | 2.38     | 5.84      | 4.32     |          |        |
| CDH23-AS1| 0.50     | 0.50     | 0.50      | 0.50     |          |        |
| CDH4     | 0.50     | 60.07    | 1643.65   | 1784.47  | Type 1   | ✓      |
| CDH5     | 0.50     | 1.34     | 10.67     | 21.09    | Type 2   | ✓      |
| CDH9     | 0.50     | 4.18     | 13.87     | 12.90    | Type 2   |        |
| CDH12    | 3.03     | 5.10     | 4.15      | 9.42     | Type 2   | ✓      |
| CDH7     | 3.03     | 1.34     | 0.50      | 4.32     | Type 2   |        |
| CDH8     | 3.03     | 4.18     | 1528.21   | 727.29   | Type 2   |        |
| CDH22    | 9.28     | 4.18     | 4.15      | 15.92    | Type 2   |        |
| CDH3     | 13.25    | 2.38     | 13.87     | 27.46    | Type 1   | ✓      |
| CDH23    | 15.09    | 19.28    | 12.21     | 83.71    |          |        |
| CDH16    | 20.53    | 5.10     | 0.50      | 0.50     | Type 1   | ✓      |
| CDH26    | 32.49    | 26.61    | 38.05     | 31.13    |          |        |
| CDH1     | 83.79    | 30.83    | 165.22    | 51.13    | Type 1   | ✓      |
| CDH15    | 262.10   | 384.90   | 127.81    | 42.07    | Type 1   |        |
| CDH10    | 273.92   | 249.01   | 15.40     | 325.80   | Type 2   |        |
| CDH11    | 337.88   | 10608.34 | 27312.83  | 20354.27 | Type 2   | ✓      |
| CDH18    | 366.09   | 34.76    | 0.50      | 292.44   | Type 2   | ✓      |
| CDH24    | 527.43   | 749.88   | 454.14    | 579.01   | Type 2   |        |
| CDH6     | 1928.67  | 547.07   | 5056.00   | 4567.14  | Type 2   |        |
| CDH13    | 8117.79  | 4106.39  | 15861.51  | 20844.73 |          |        |
| CDH2     | 21088.44 | 1784.05  | 19865.16  | 25270.92 | Type 1   | ✓      |

FIG. 19E

```
                          SEQUENCE LISTING

<160> NUMBER OF SEQ ID NOS: 5

<210> SEQ ID NO 1
<211> LENGTH: 457
<212> TYPE: PRT
<213> ORGANISM: Homo sapiens

<400> SEQUENCE: 1

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
            115                 120                 125

Pro Gln Gln Asn Gly Gln Pro Leu Arg Pro Leu Val Pro Asp Ala Ser
        130                 135                 140

Lys Gln Arg Leu Met Glu Asn Thr Glu Asp Trp Arg Pro Arg Pro Gly
145                 150                 155                 160

Thr Gly Gln Ser Arg Ser Phe Arg Ile Leu Ala His Leu Thr Gly Thr
                165                 170                 175

Glu Phe Met Gln Asp Pro Asp Glu Glu His Leu Lys Lys Ser Ser Gln
            180                 185                 190

Val Pro Arg Thr Glu Ala Pro Ala Pro Ala Ser Ser Thr Pro Gln Glu
        195                 200                 205

Pro Trp Pro Gly Pro Thr Ala Pro Ser Pro Thr Ser Arg Pro Pro Trp
    210                 215                 220

Ala Val Asp Pro Ala Phe Ala Glu Arg Tyr Ala Pro Asp Lys Thr Ser
225                 230                 235                 240

Thr Val Leu Thr Arg His Ser Gln Pro Ala Thr Pro Thr Pro Leu Gln
                245                 250                 255

Ser Arg Thr Ser Ile Val Gln Ala Ala Ala Gly Gly Val Pro Gly Gly
            260                 265                 270

Gly Ser Asn Asn Gly Lys Thr Pro Val Cys His Gln Cys His Lys Val
        275                 280                 285

Ile Arg Gly Arg Tyr Leu Val Ala Leu Gly His Ala Tyr His Pro Glu
    290                 295                 300

Glu Phe Val Cys Ser Gln Cys Gly Lys Val Leu Glu Glu Gly Gly Phe
305                 310                 315                 320

Phe Glu Glu Lys Gly Ala Ile Phe Cys Pro Pro Cys Tyr Asp Val Arg
                325                 330                 335

Tyr Ala Pro Ser Cys Ala Lys Cys Lys Lys Lys Ile Thr Gly Glu Ile
```

```
            340                 345                 350
Met His Ala Leu Lys Met Thr Trp His Val His Cys Phe Thr Cys Ala
            355                 360                 365

Ala Cys Lys Thr Pro Ile Arg Asn Arg Ala Phe Tyr Met Glu Glu Gly
        370                 375                 380

Val Pro Tyr Cys Glu Arg Asp Tyr Glu Lys Met Phe Gly Thr Lys Cys
385                 390                 395                 400

His Gly Cys Asp Phe Lys Ile Asp Ala Gly Asp Arg Phe Leu Glu Ala
                405                 410                 415

Leu Gly Phe Ser Trp His Asp Thr Cys Phe Val Cys Ala Ile Cys Gln
            420                 425                 430

Ile Asn Leu Glu Gly Lys Thr Phe Tyr Ser Lys Lys Asp Arg Pro Leu
        435                 440                 445

Cys Lys Ser His Ala Phe Ser His Val
    450                 455

<210> SEQ ID NO 2
<211> LENGTH: 790
<212> TYPE: PRT
<213> ORGANISM: Homo sapiens

<400> SEQUENCE: 2

Met Lys Ile Thr Ser Thr Ser Cys Ile Cys Pro Val Leu Val Cys Leu
1               5                   10                  15

Cys Phe Val Gln Arg Cys Tyr Gly Thr Ala His His Ser Ser Ile Lys
            20                  25                  30

Val Met Arg Asn Gln Thr Lys His Ile Glu Gly Glu Thr Glu Val His
        35                  40                  45

His Arg Pro Lys Arg Gly Trp Val Trp Asn Gln Phe Phe Val Leu Glu
    50                  55                  60

Glu His Met Gly Pro Asp Pro Gln Tyr Val Gly Lys Leu His Ser Asn
65                  70                  75                  80

Ser Asp Lys Gly Asp Gly Ser Val Lys Tyr Ile Leu Thr Gly Glu Gly
                85                  90                  95

Ala Gly Thr Ile Phe Ile Ile Asp Asp Thr Thr Gly Asp Ile His Ser
            100                 105                 110

Thr Lys Ser Leu Asp Arg Glu Gln Lys Thr His Tyr Val Leu His Ala
        115                 120                 125

Gln Ala Ile Asp Arg Arg Thr Asn Lys Pro Leu Glu Pro Glu Ser Glu
    130                 135                 140

Phe Ile Ile Lys Val Gln Asp Ile Asn Asp Asn Ala Pro Lys Phe Thr
145                 150                 155                 160

Asp Gly Pro Tyr Ile Val Thr Val Pro Glu Met Ser Asp Met Gly Thr
                165                 170                 175

Ser Val Leu Gln Val Thr Ala Thr Asp Ala Asp Asp Pro Thr Tyr Gly
            180                 185                 190

Asn Ser Ala Arg Val Val Tyr Ser Ile Leu Gln Gly Gln Pro Tyr Phe
        195                 200                 205

Ser Val Asp Pro Lys Thr Gly Val Ile Arg Thr Ala Leu His Asn Met
    210                 215                 220

Asp Arg Glu Ala Arg Glu His Tyr Ser Val Val Ile Gln Ala Lys Asp
225                 230                 235                 240

Met Ala Gly Gln Val Gly Gly Leu Ser Gly Ser Thr Thr Val Asn Ile
                245                 250                 255
```

-continued

```
Thr Leu Thr Asp Val Asn Asp Asn Pro Pro Arg Phe Pro Gln Lys His
            260                 265                 270
Tyr Gln Leu Tyr Val Pro Glu Ser Ala Gln Val Gly Ser Ala Val Gly
        275                 280                 285
Lys Ile Lys Ala Asn Asp Ala Asp Thr Gly Ser Asn Ala Asp Met Thr
    290                 295                 300
Tyr Ser Ile Ile Asn Gly Asp Gly Met Gly Ile Phe Ser Ile Ser Thr
305                 310                 315                 320
Asp Lys Glu Thr Arg Glu Gly Ile Leu Ser Leu Lys Lys Pro Leu Asn
                325                 330                 335
Tyr Glu Lys Lys Lys Ser Tyr Thr Leu Asn Ile Glu Gly Ala Asn Thr
            340                 345                 350
His Leu Asp Phe Arg Phe Ser His Leu Gly Pro Phe Lys Asp Ala Thr
        355                 360                 365
Met Leu Lys Ile Ile Val Gly Asp Val Asp Glu Pro Pro Leu Phe Ser
    370                 375                 380
Met Pro Ser Tyr Leu Met Glu Val Tyr Glu Asn Ala Lys Ile Gly Thr
385                 390                 395                 400
Val Val Gly Thr Val Leu Ala Gln Asp Pro Asp Ser Thr Asn Ser Leu
                405                 410                 415
Val Arg Tyr Phe Ile Asn Tyr Asn Val Glu Asp Asp Arg Phe Phe Asn
            420                 425                 430
Ile Asp Ala Asn Thr Gly Thr Ile Arg Thr Thr Lys Val Leu Asp Arg
        435                 440                 445
Glu Glu Thr Pro Trp Tyr Asn Ile Thr Val Thr Ala Ser Glu Ile Asp
    450                 455                 460
Asn Pro Asp Leu Leu Ser His Val Thr Val Gly Ile Arg Val Leu Asp
465                 470                 475                 480
Val Asn Asp Asn Pro Pro Glu Leu Ala Arg Glu Tyr Asp Ile Ile Val
                485                 490                 495
Cys Glu Asn Ser Lys Pro Gly Gln Val Ile His Thr Ile Ser Ala Thr
            500                 505                 510
Asp Lys Asp Asp Phe Ala Asn Gly Pro Arg Phe Asn Phe Phe Leu Asp
        515                 520                 525
Glu Arg Leu Pro Val Asn Pro Asn Phe Thr Leu Lys Asp Asn Glu Asp
    530                 535                 540
Asn Thr Ala Ser Ile Leu Thr Arg Arg Arg Phe Ser Arg Thr Val
545                 550                 555                 560
Gln Asp Val Tyr Tyr Leu Pro Ile Met Ile Ser Asp Gly Gly Ile Pro
                565                 570                 575
Ser Leu Ser Ser Ser Thr Leu Thr Ile Arg Val Cys Ala Cys Glu
            580                 585                 590
Arg Asp Gly Arg Val Arg Thr Cys His Ala Glu Ala Phe Leu Ser Ser
        595                 600                 605
Ala Gly Leu Ser Thr Gly Ala Leu Ile Ala Ile Leu Cys Val Leu
    610                 615                 620
Ile Leu Leu Ala Ile Val Val Leu Phe Ile Thr Leu Arg Arg Ser Lys
625                 630                 635                 640
Lys Glu Pro Leu Ile Ile Ser Glu Glu Asp Val Arg Glu Asn Val Val
                645                 650                 655
Thr Tyr Asp Asp Glu Gly Gly Gly Glu Asp Thr Glu Ala Phe Asp
            660                 665                 670
Ile Thr Ala Leu Arg Asn Pro Ser Ala Ala Glu Glu Leu Lys Tyr Arg
```

```
                675                 680                 685
Arg Asp Ile Arg Pro Glu Val Lys Leu Thr Pro Arg His Gln Thr Ser
        690                 695                 700

Ser Thr Leu Glu Ser Ile Asp Val Gln Glu Phe Ile Lys Gln Arg Leu
705                 710                 715                 720

Ala Glu Ala Asp Leu Asp Pro Ser Val Pro Pro Tyr Asp Ser Leu Gln
                725                 730                 735

Thr Tyr Ala Tyr Glu Gly Gln Arg Ser Glu Ala Gly Ser Ile Ser Ser
            740                 745                 750

Leu Asp Ser Ala Thr Thr Gln Ser Asp Gln Asp Tyr His Tyr Leu Gly
        755                 760                 765

Asp Trp Gly Pro Glu Phe Lys Lys Leu Ala Glu Leu Tyr Gly Glu Ile
    770                 775                 780

Glu Ser Glu Arg Thr Thr
785                 790

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagattactt tgctgcctta a                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcgagactat gagaagatgt t                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
cgtctgtgcg atatgtcaga t                                             21
```

ENIGMA AND CDH18 AS COMPANION DIAGNOSTICS FOR CDK4 INHIBITORS

PRIORITY CLAIM

This application is a National Stage Application of International Application No. PCT/US2017/021560, filed Mar. 9, 2017, which claims the benefit of and priority to U.S. Provisional Application Ser. No. 62/306,000, filed Mar. 9, 2016, the entire contents of which are hereby incorporated by reference.

GRANT INFORMATION

This invention was made with government support under grant number CA140146 awarded by the National Institutes of Health. The government has certain rights in the invention.

SEQUENCE LISTING

The instant application contains a Sequence Listing which has been submitted electronically in ASCII format and is hereby incorporated by reference in its entirety. Said, ASCII copy, created on Dec. 10, 2018 is named 115872-0437 SL.txt and is 11,790 bytes in size.

1. INTRODUCTION

This present invention relates to biomarkers that can be used to evaluate the likelihood that a CDK4 inhibitor would produce an anti-cancer effect in a subject. As such, these biomarkers may be used in methods of treating cancer patients.

2. BACKGROUND OF THE INVENTION

CDK4 inhibition therapies are currently in numerous U.S. clinical trials for several cancers including liposarcoma, ER-positive HER2-negative breast cancer, lung cancer, multiple myeloma and glioblastoma. Although patients typically are pre-screened for genetic lesions that would render their disease responsive to the drug (i.e., Rb protein expression, CDK4 amplification or loss of CDKN2A depending on the trial), responsiveness to therapy is nonetheless uncertain. For example, in the Phase II trial testing a CDK4/6 inhibitor in patients with CDK4-amplified liposarcoma carried out at Memorial Sloan-Kettering Cancer Center, approximately 66% of patients achieved progression-free survival that met the trial criteria, including 3% of patients achieving partial response according to RECIST (Response Evaluation Criteria In Solid Tumors) and 63% achieving stable disease. An additional 31% of patients had progressive disease while being treated with the drug, indicating that predicting whether patients will respond to CDK4 therapy is problematic. As of March 2017, only one CDK4 inhibitor, palbociclib, has received FDA approval so use of CDK4 inhibitors would not be regarded as standard therapy.

PDZ and LIM Domain 7 (PDLIM7), which is also known as "Enigma", is a member of the PDZ-LIM family of proteins and includes 1 PDZ domain and 3 LIM domains (see FIG. 2). Enigma has been shown to interact with 5 proteins including Ret/Ptc2, Protein Kinase C (PKC) and the insulin receptor (InsR) (FIG. 2, and see Durick et al., Mol. and Cell. Bio. 18(4):2298-2308 (1998); Kuroda et al., J. Biol. Chem. 271:31029-31032 (1996); Wu et al., J. Biol. Chem. 271:15934-15941 (1996); and Jung et al., J. of Clinical Investigation 120(12):4493-4506 (2010)). In addition, it was previously shown that Enigma binds to MDM2 and the binding of MDM2 and Enigma blocks MDM2 autoubiquitination (Jung et al. (2010)). However, the mechanism by which Enigma regulates MDM2 autoubiquitination during senescence is currently unknown.

3. SUMMARY OF THE INVENTION

The present invention relates to methods and compositions that provide a companion diagnostic for CDK4 inhibitors, and for related methods of treating patients. In particular, the present invention relates to the use of Enigma and/or Cadherin 18 ("CDH18") as biomarkers for evaluating whether a cancer can be successfully treated by CDK4 inhibition. It is based, at least in part, on the discovery that treatment with a CDK4 inhibitor is more effective where treated cancer cells undergo cellular senescence rather than a transient cell cycle arrest, where MDM2 turnover plays a role in the induction of senescence within CDK4 inhibitor treated cells, where cells that are responsive to treatment with a CDK4 inhibitor are associated with the localization of Enigma and/or CDH18 to foci within the cells and (2) higher levels of expression of CDH18 in cells responsive to CDK4 inhibition.

4. BRIEF DESCRIPTION OF THE FIGURES

FIG. 3A-D shows the effects of knockdown of Enigma in the non-responder cell line LS8107 following CDK4 inhibition; "En638" denotes knockdown; "scr" denotes negative control; and (+) denotes treatment with CDK4 inhibitor PD0332991. (A) shows the percent SA-β-Gal; (B) shows percent HP1γ foci; (C) shows the average ATRX foci per cell; and (D) shows expression levels of Enigma and MDM2 in the context of knockdown (En638 treatment) and treatment with CDK4 inhibitor.

Figures 4A, 4B:
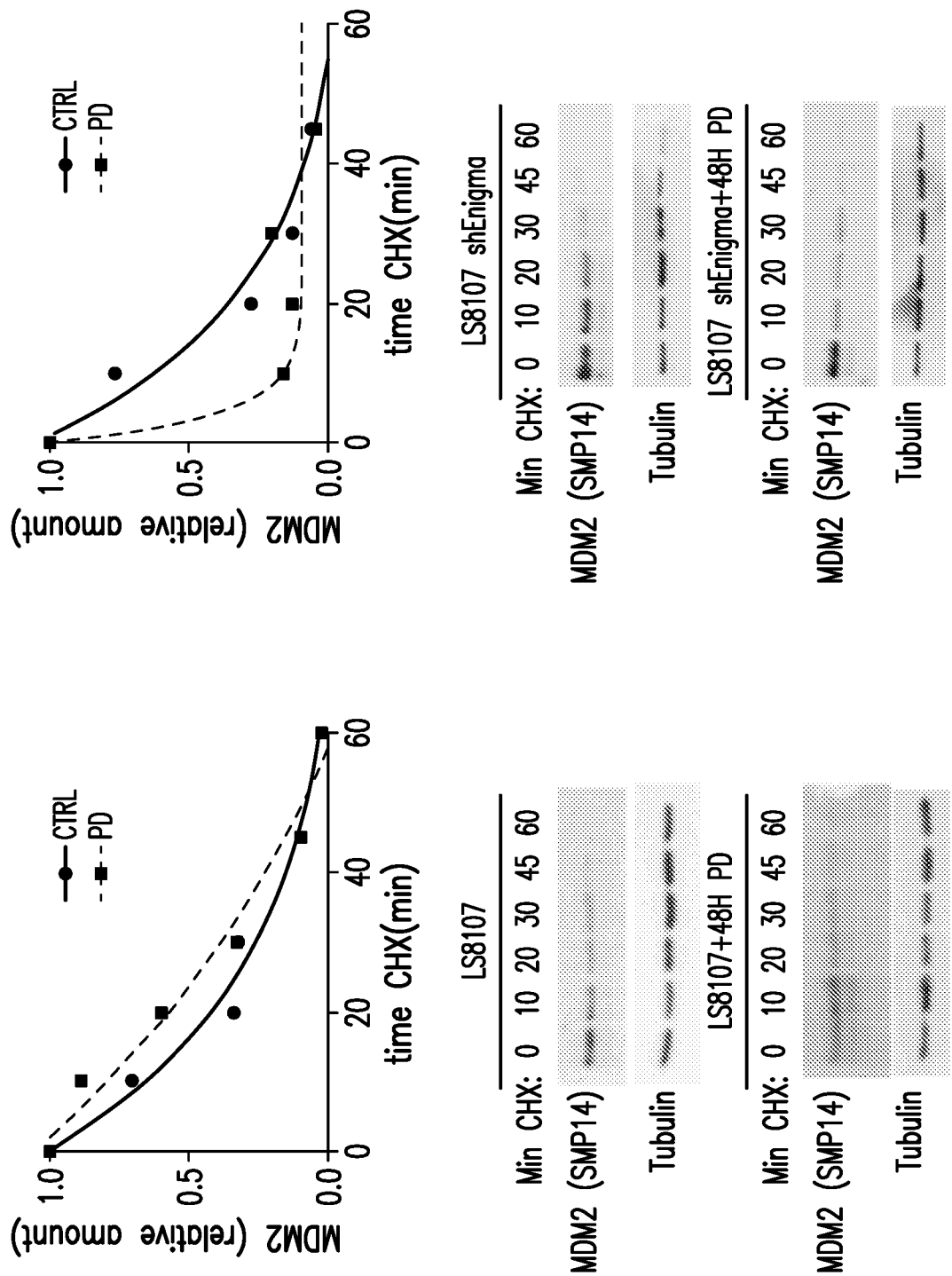

FIG. 4A-B shows the effect of (B) knockdown of Enigma on the degradation of MDM2 following CDK4 inhibition in non-responder cells LS8107 cells. (A) shows corresponding results in LS8107 cells without knockdown.

Figures 5A, 5B, 5C:
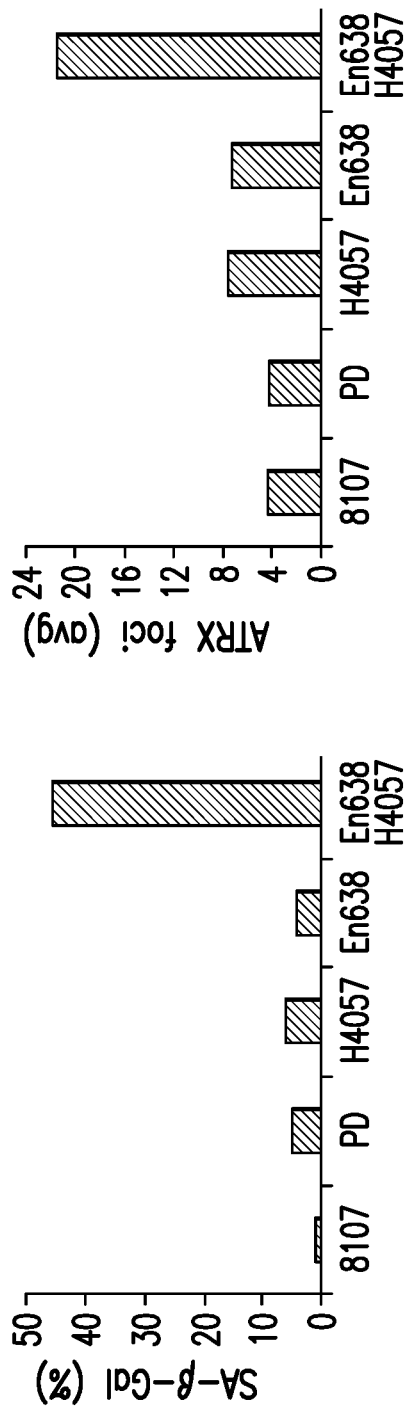

FIG. 5A-C shows the knockdown of Enigma, HAUSP, and both Enigma and HAUSP in non-responder cells. (A) shows the percent SA-β-Gal; (B) shows the average ATRX foci per cell; and (C) shows expression of HAUSP and Enigma in the various knockdown experiments.

Figure 6:
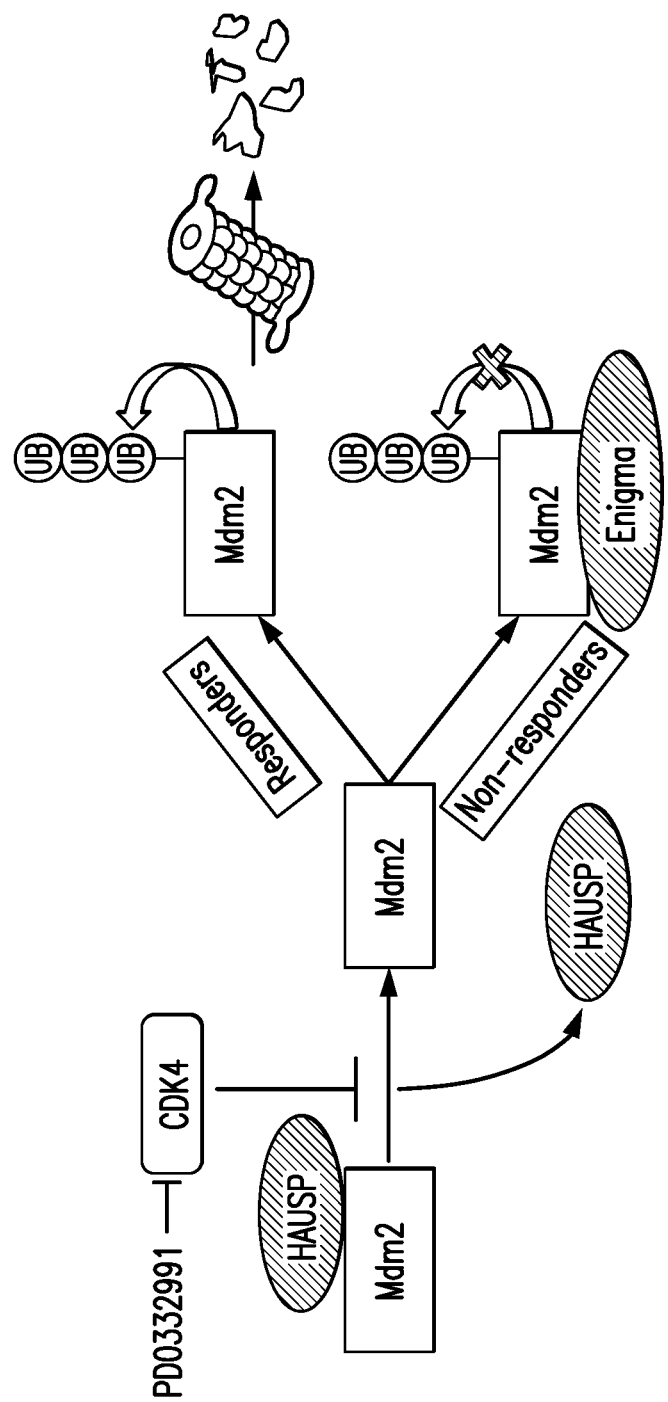

FIG. 6 depicts a schematic showing the effect Enigma may have on MDM2 autoubiquitination.

FIG. 7A-C shows the immunoprecipitation of Enigma and MDM2 in (A) non-responder LS8107 and responder LS8817 cells and (B) H358 cells. (C) shows the protein levels of Enigma across various responder and non-responder cell lines.

Figure 8:
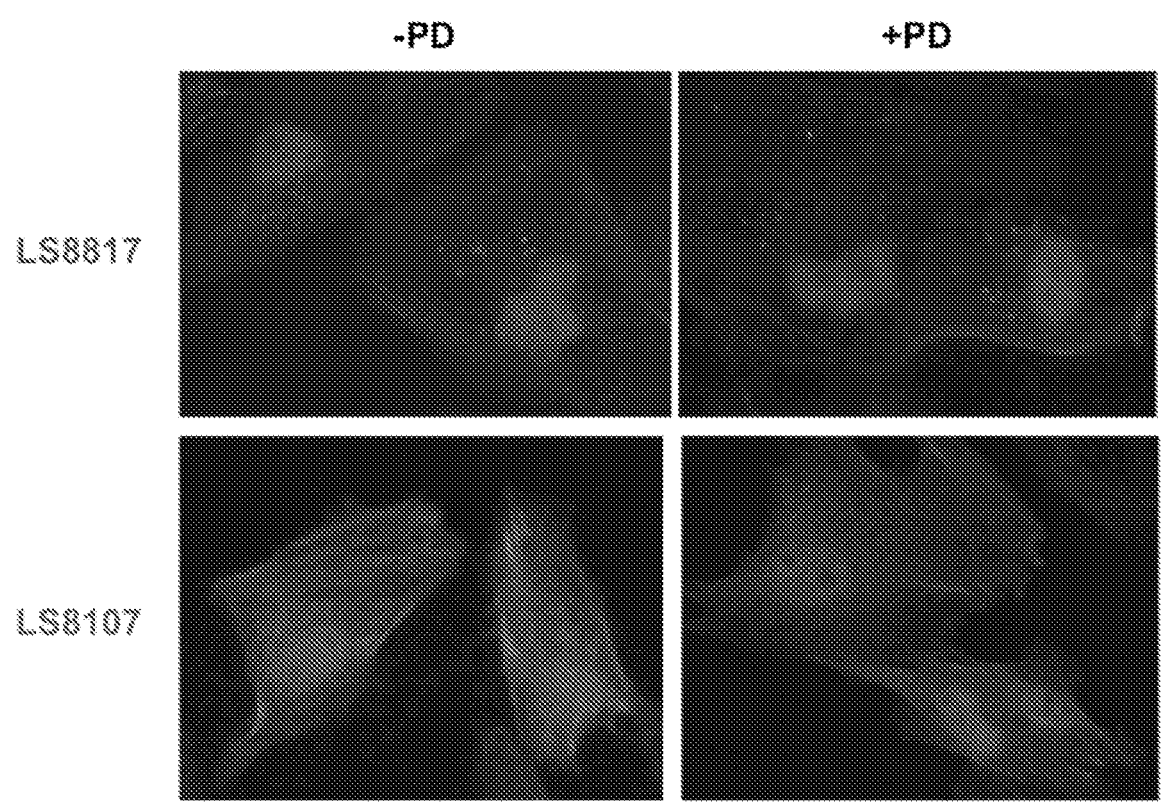

FIG. 8 shows the localization of Enigma in non-responder LS8107 and responder LS8817 cells.

Figure 9:
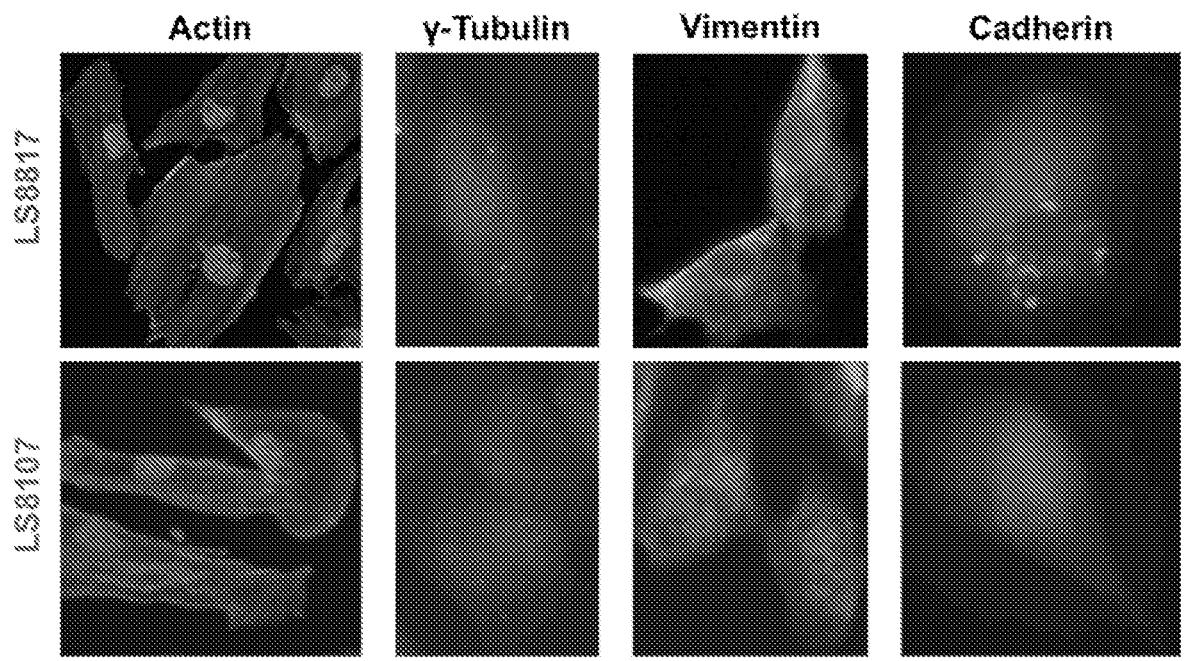

FIG. 9 shows the immunofluorescence of Actin, γ-tubulin. Vimentin and cadherin in non-responder LS8107 and responder LS8817 cells.

Figure 10:
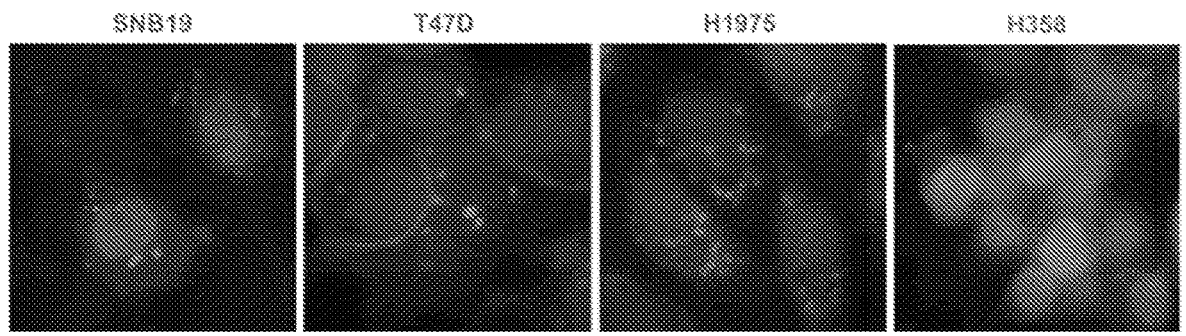

FIG. 10 shows the localization of cadherin in glioma (SNB19), breast (T47D) and non-small cell lung cancer (NSCLC) responder (H1975) cell lines and in a non-responder NSCLC (H358) cell line.

Figure 11:
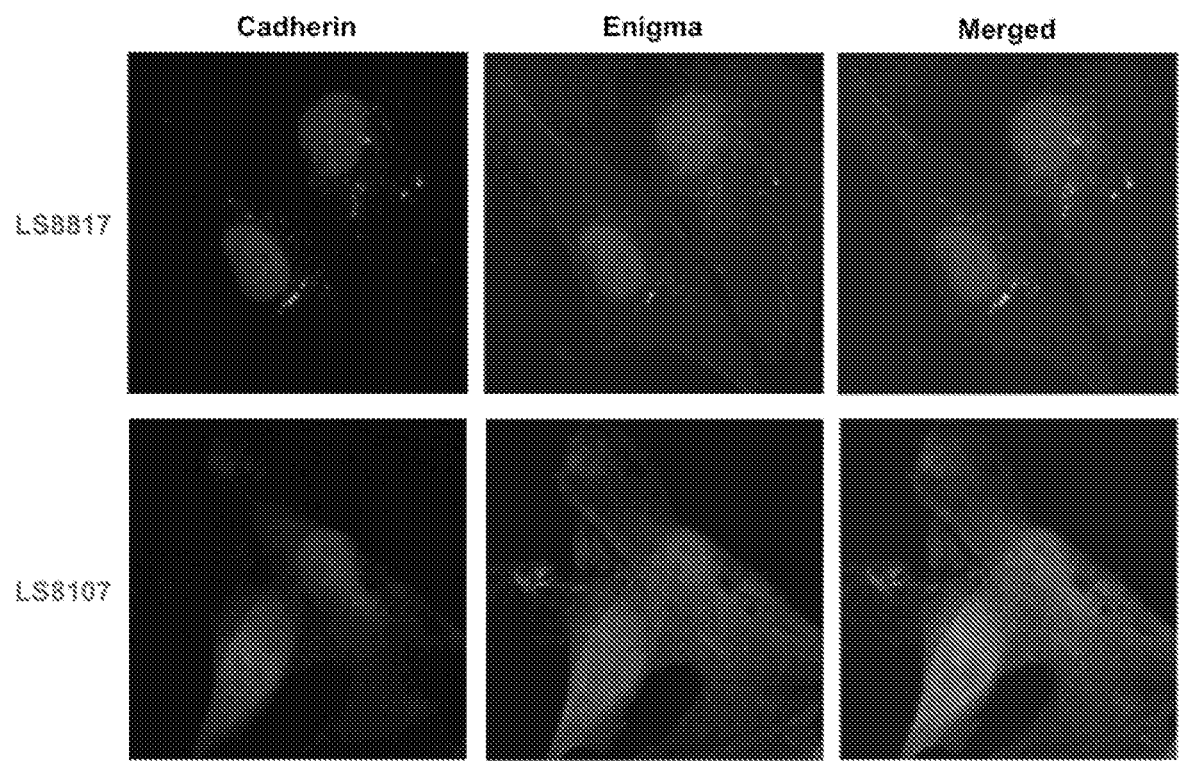

FIG. 11 shows the localization of Enigma and cadherin in responder LS8817 and non-responder LS8107 cells.

FIG. 12 shows the localization of Enigma and cadherin in responder LS8817 and non-responder LS8107 cells using the proximity ligation assay.

FIG. 13A-D shows the localization of cadherin in responder cells upon serum starvation. (A) shows the percent SA-β-Gal in cells cultured in 10% or 0.5% serum or treated with CDK4 inhibitor PD0332991; (B) shows MDM2 protein levels in the various growth conditions; (C) shows loss of foci with serum starvation (0.5% serum); and (D) shows interaction between Enigma and MDM2 in the serum-starved cells.

Figure 14:
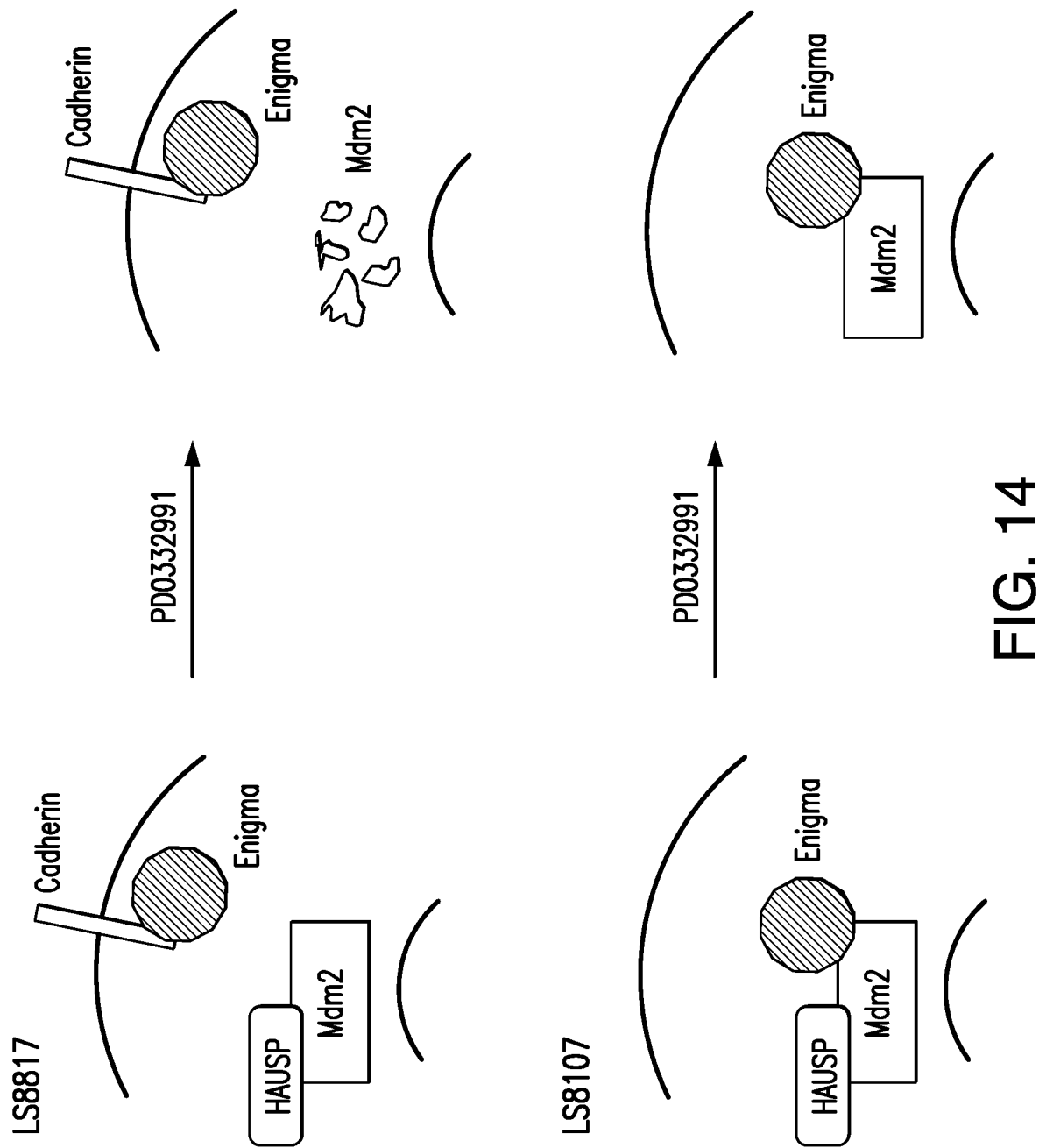

FIG. 14 depicts a schematic showing the interaction between cadherin, Enigma and MDM2 in responder and non-responder cells upon treatment with a CDK4 inhibitor.

Figure 15:
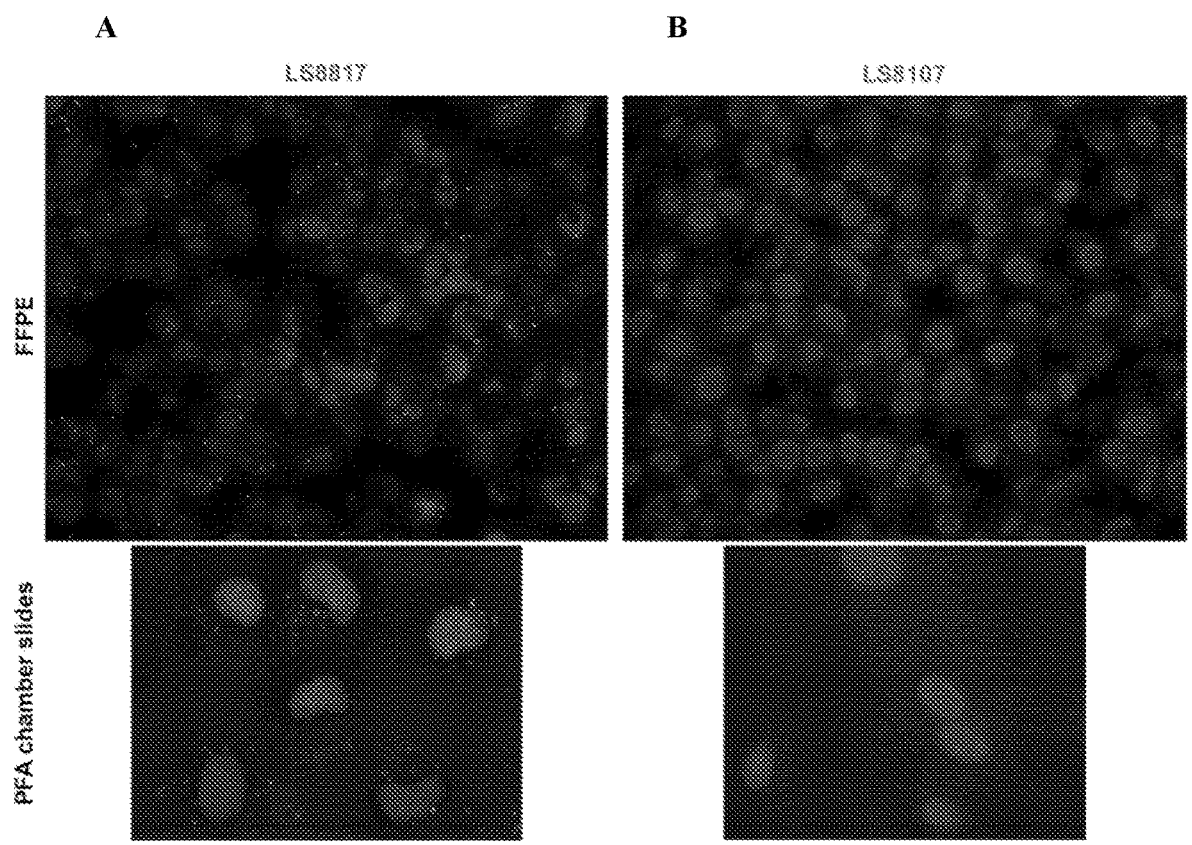

FIG. 15A-B shows the localization of Enigma and cadherin using the proximity ligation assay in (A) responder LS8817 cells and (B) non-responder LS8107 cells fixed by the formalin fixed paraffin embedded method. Smaller photos in lower panels are magnified views.

Figure 16:
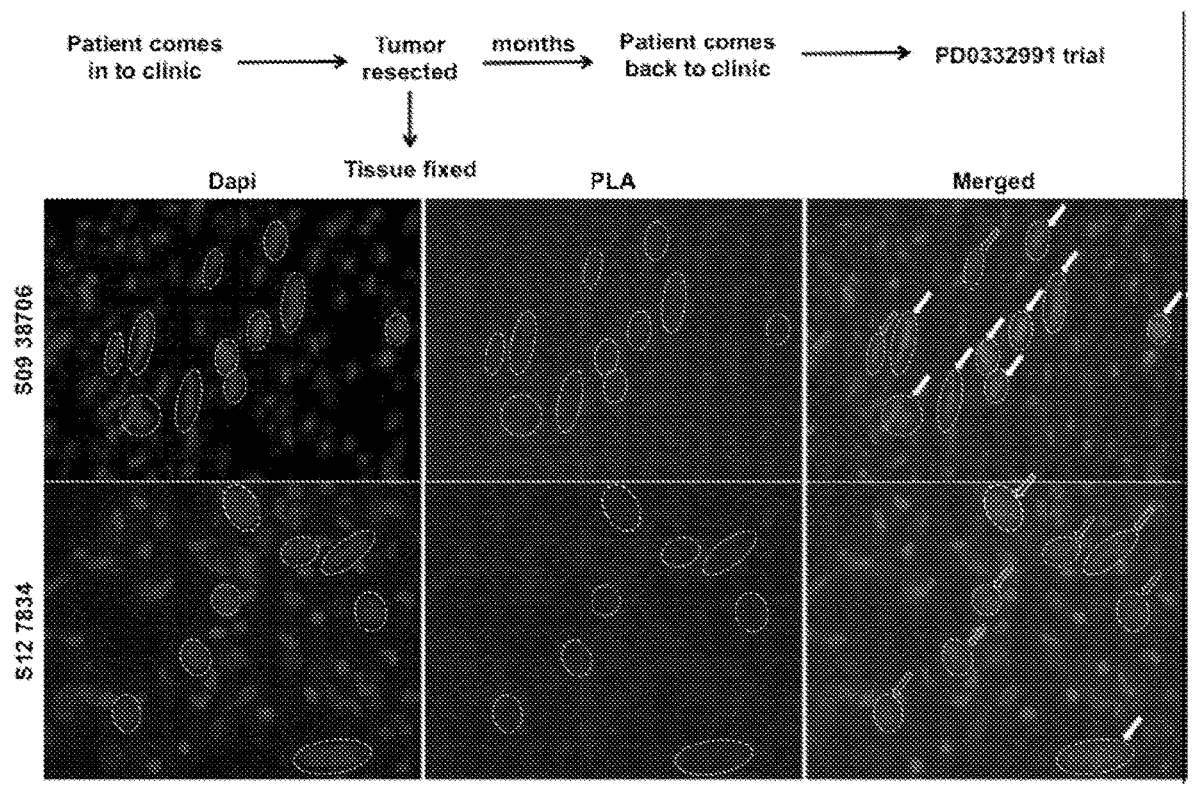

FIG. 16 shows the localization of Enigma and cadherin in patient samples using a proximity ligation assay.

Figure 17:
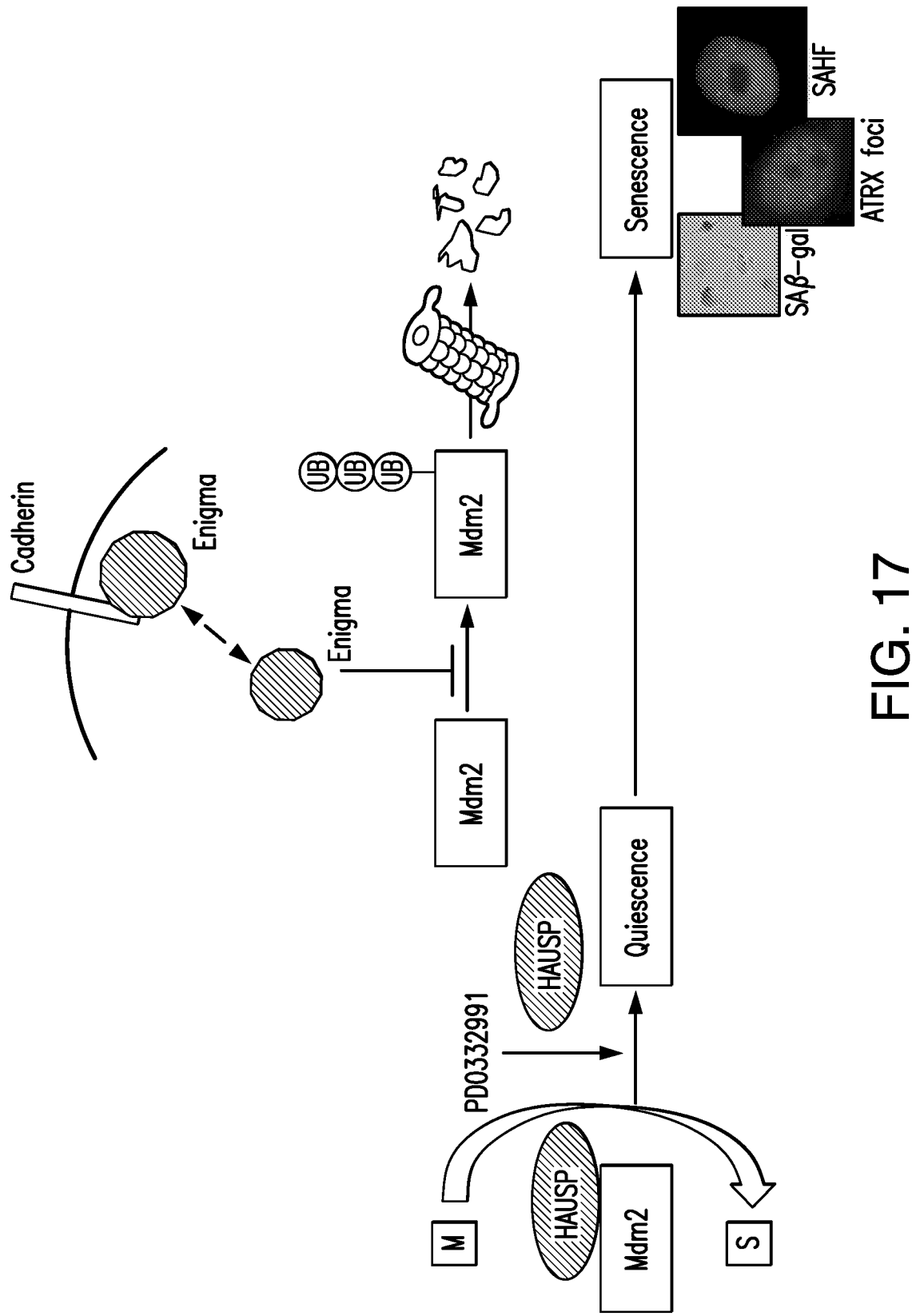

FIG. 17 depicts a schematic showing the interaction between cadherin, Enigma, HAUSP and MDM2 in responder and non-responder cells upon treatment with a CDK4 inhibitor.

Figure 18:
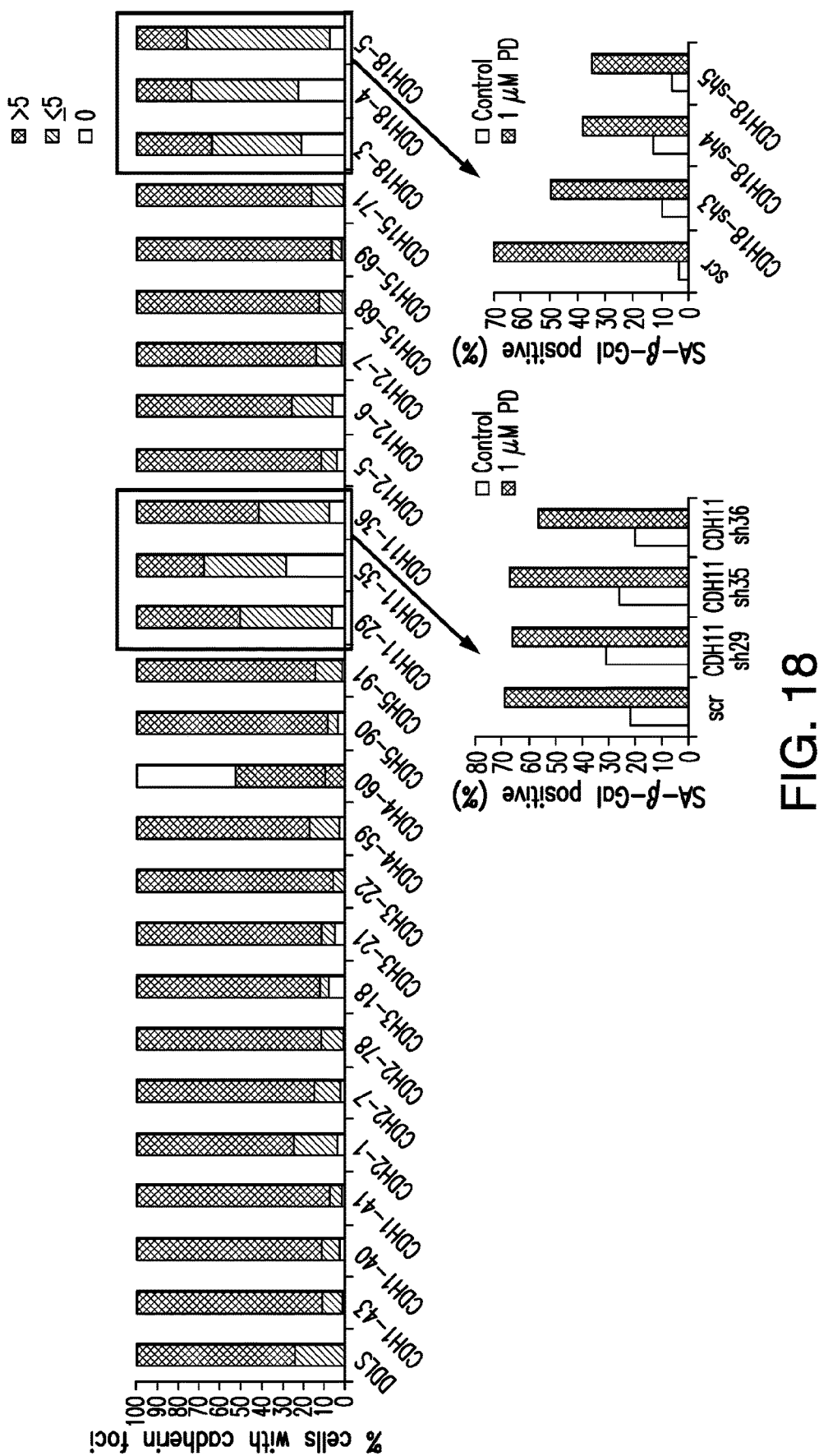

FIG. 18 shows knockdown of various cadherins (CDH1, CDH2, CDH3, CDH4, CDH5, CDH11, CDH12, CDH15, CDH16 and CDH18) by shRNA and its effects on the reduction of foci.

FIG. 19A-E shows (A) a schematic showing a proposed model of the functional relationship between CDH18, Enigma (PDLIM7) and the ubiquination of MDM2. (B) shows a map of CDH18. (C) shows higher levels of CDH18 expression in responder cell lines LS8817, LS141, and H1975 relative to non-responder cell lines LS8107, LS8313, and H358. (D) shows imaging studies of CDH18 in LS8817, LS8107 and H1975 cell lines. (E) shows mRNA expression levels of various cadherin species, showing substantially higher expression levels of CDH18 in responder cell lines LS8817 and LS7785-1 relative to non-responder cell lines LS8107 and LS7785-10.

5. DETAILED DESCRIPTION OF THE INVENTION

For clarity and not by way of limitation the detailed description of the invention is divided into the following subsections:
(i) Biomarkers;
 (a) Enigma as a biomarker;
 (b) CDH18 as a biomarker; and
 (c) Methods of detection;
(ii) CDK4 inhibitors;
(iii) Enigma inhibitors;
(iv) Cancer targets;
(v) Methods of use; and
(vi) Kits.

5.1 Biomarkers

The present invention discloses biomarkers that can be used to determine if a cancer will be more likely to respond to treatment with a CDK4 inhibitor. In certain embodiments, the biomarkers of the present disclosure can be used to determine if it is more likely that a CDK4 inhibitor will have an anti-cancer effect on a cancer. In certain embodiments, one or both of the disclosed biomarkers, can be analyzed in a cancer to determine if the cancer will be more likely to respond to treatment with a CDK4 inhibitor.

5.1.1 Enigma as a Biomarker

PDZ And LIM Domain 7 (PDLIM7) is also referred to herein as Enigma.

The present invention discloses Enigma as a biomarker.

The present invention discloses Enigma foci as a biomarker for cells that are more likely to respond to treatment with a CDK4 inhibitor. The term "Enigma foci," as used herein, refers to Enigma-positive punctate structures that can be visualized within a cell.

In a specific, non-limiting embodiment, Enigma foci may be detected using an immunodetection reagent specific for an Enigma protein for example but not by limitation, an antibody sold by Santa Cruz Biotechnology as Cat. No. SC-98370 (H110; "the '370 Ab"), a fragment thereof, or an antibody that competitively inhibits binding of the '370 Ab to human Enigma protein.

In a specific, non-limiting embodiment, an Enigma protein may be a human Enigma protein having the amino acid sequence as set forth in NCBI database accession no. AAF76152.1, which is disclosed below as SEQ ID NO: 1.

[SEQ ID NO: 1]
mdsfkvvlegpapwgfrlqggkdfnvplsisrltpggkaaqagvavgdwv lsidgenagslthieaqnkiracgerlslglsraqpvqskpqkasapaad pprytfapsyslnktarpfgapppadsapqqngqplrplvpdaskqrlme ntedwrprpgtgqsrsfrilahltgtefmqdpdeehlkkssqvprteapa passtpqepwpgptapsptsrppwavdpafaeryapdktstvltrhsqpa tptplqsrtsivqaaaggvpgggsnngktpvchqchkvirgrylvalgha yhpeefvcsqcgkvleeggffeekgaifcppcydvryapscakckkkitg eimhalkmtwhvhcftcaacktpirnrafymeegvpycerdyekmfgtkc hgcdfkidagdrflealgfswhdtcfvcaicqinlegktfyskkdrplck shafshv Enigma proteins for non-human species are known or can be determined according to methods known in the art, for example, where the sequence is the allele represented in the majority of the population.

In a specific, non-limiting embodiment, an Enigma protein may be a mouse Enigma protein having the amino acid sequence as set forth in NCBI database accession no. AAH52698.1.

In a specific, non-limiting embodiment, an Enigma protein may be a rat Enigma protein having the amino acid sequence as set forth in NCBI database accession no. NP 775148.1.

5.1.2 CDH18 as a Biomarker

The present invention discloses CDH18 as a biomarker.

The present invention discloses CDH18 foci as a biomarker for cells that are more likely to respond to treatment with a CDK4 inhibitor. The term "CDH18 foci," as used herein, refers to CDH18-positive punctate structures that can be visualized within a cell, e.g., visualized within a cell using a CDH18-specific antibody, for example but not by limitation, an antibody sold by SIGMA as Catalog #WH0001016M1 ("the '6M1 antibody"; which was raised to CDH18 (NP_004925 a.a. 467-577 fused to GST)), a fragment thereof, or an antibody that competitively inhibits binding of the '6M1 antibody to CDH18. Alternatively, an antibody sold by BD Biosciences, Cat. No. 610181 ("the '181 Ab"), a fragment thereof, or an antibody that competitively inhibits binding of the '181 Ab to CDH18 may be used (the '181 Ab is offered as an anti-cadherin E antibody, but cross-reacts with CDH18).

In a specific, non-limiting embodiment, CDH18 foci may be detected using an immunodetection reagent specific for CDH18, such as the 6M1 antibody or fragment referred to above.

In non-limiting embodiments, a CDH18 biomarker can be a protein that is detectably present using the '6M1 antibody, a fragment thereof, or an antibody that competitively inhibits binding of the '6M1 antibody to CDH18.

In a specific, non-limiting embodiment, a CDH18 protein may be a human CDH18 protein having the amino acid sequence as set forth in NCBI Reference Seq. NP_004925 which is set forth below as SEQ ID NO: 2.

[SEQ ID NO: 2]
mkitstscicpvlvclcfvqrcygtahhssikvmrnqtkhiegetevhhr pkrgwvwnqffvleehmgpdpqyvgklhsnsdkgdgsvkyiltgegagti fiiddttgdihstksldreqkthyvlhaqaidrrtnkplepesefiikvq dindnapkftdgpyivtvpemsdmgtsvlqvtatdaddptygnsarvvys ilqgqpyfsvdpktgvirtalhnmdrearehysvviqakdmagqvgglsg sttvnitltdvndnpprfpqkhyqlyvpesaqvgsavgkikandadtgsn admtysiingdgmgifsistdketregilslkkpinyekkksytlniega nthldfrfshlgpfkdatmlkiivgdvdepplfsmpsylmevyenakigt vvgtvlaqdpdstnslvryfinynveddrffnidantgtirttkvldree tpwynitvtaseidnpdlls hvtvgirvldvndnppelareydiivcenskpgqvihtisatdkddfang prfnfflderlpvnpnftlkdnedntasiltrrrrfsrtvqdvyylpimi sdggipslssssttltirvcacerdgrvrtchaeaflssaglstgaliail lcvlillaivvlfitlrrskkepliiseedvrenvvtyddegggeedtea fditalrnpsaaeelkyrrdirpevkltprhqtsstlesidvqefikqrl aeadldpsvppydslqtyayegqrseagsissldsattqsdqdyhylgdw gpefkklaelygeiesertt CDH18 proteins for non-human species are known or can be determined according to methods known in the art, for example, where the sequence is the allele represented in the majority of the population.

In a specific, non-limiting embodiment, a CDH18 protein may be a mouse CDH18 protein having the amino acid sequence as set forth in NCBI database accession no. NP_001074768.1. In a specific, non-limiting embodiment, a CDH18 protein may be a rat CDH18 protein having the amino acid sequence as set forth in NCBI database accession no. XP_017446691.1.

Alternatively, a CDH18 mRNA level may be a biomarker according to the invention (see FIG. 19E). CDH18 mRNA levels may be evaluated using CDH18-encoding nucleic acid sequences and methods known in the art. As a non-limiting example, the level of human CDH18 mRNA may be assessed. where the sequence of CDH18 cDNA is as set forth in NCBI Reference Sequence NM 004934.3.

5.1.3 Methods of Detection

Methods for determining the localization of a protein biomarker, e.g., Enigma or CDH18, include, but are not limited to, immunofluorescence, immunoglobulin-mediated assays and other techniques known in the art.

In certain, non-limiting embodiments, immunohistochemistry can be used for detecting an Enigma and/or a CDH18 biomarker. For example, a first antibody, e.g., an antibody specific for Enigma or CDH18, can be brought into contact with a sample, e.g., a cell or a thin layer of cells, followed by washing to remove unbound antibody, and then contacted with a second, labeled antibody. Labeling can be by fluorescent markers, enzymes, such as peroxidase, avidin or radiolabeling. In certain embodiments, the first antibody can be conjugated to a fluorophore for direct detection. The labeling can be analyzed visually using microscopy and the results can be recorded. In certain embodiments, immunohistochemistry can be performed to detect a combination of an Enigma and a CDH18 biomarkers in the same sample to determine whether the biomarkers colocalize. The term "colocalize" as used herein refers to Enigma and/or CDH18 occurring in close proximity to each other. In certain embodiments, colocalization of two proteins, e.g., two biomarkers, refers to two proteins that reside within about less than 100 nm of each other in a cell. In certain embodiments, the two proteins reside within about 40 nm of each other in a cell.

In certain embodiments, a proximity ligation assay can be used to determine colocalization of CDH18 and Enigma within a cell. Non-limiting examples of proximity ligation assays are disclosed in U.S. Publication Nos. 2002/0064779, 2005/0003361 and 2008/0293051. For example, and not by way of limitation, a proximity ligation assay for use in the present invention can comprise contacting a sample, e.g., one or more cells of a cancer, with a first primary antibody and a second primary antibody, e.g., the first primary antibody is specific for CDH18 and the second primary antibody is specific for Enigma. In non-limiting embodiments, the primary antibody specific for CDH18 can be the '6M1 antibody referred to above, a fragment thereof, or an antibody that competitively inhibits binding of the '6M1 Ab to CDH18. In certain embodiments, the first and second primary antibodies are of different species. The sample can be further contacted with a first secondary antibody and a second secondary antibody, where the first secondary antibody is specific for the first primary antibody and the second secondary antibody is specific for the second primary antibody. In certain embodiments, the first and second secondary antibodies are conjugated to different oligonucleotide probes, which are complementary to each other. If the two secondary antibodies are within about 40 nm of each other, the oligonucleotides on each secondary antibody can ligate to one another and be further amplified, which can be detected by immunofluorescence.

Various automated sample processing, scanning and analysis systems suitable for use with immunohistochemistry are available in the art. Such systems can include automated staining (see, e.g., the Benchmark system, Ventana Medical Systems, Inc.) and microscopic scanning, computerized image analysis, serial section comparison (to control for variation in the orientation and size of a sample), digital report generation, and archiving and tracking of samples (such as slides on which tissue sections are placed). Cellular imaging systems are commercially available that combine conventional light microscopes with digital image processing systems to perform quantitative analysis on cells and tissues, including immunostained samples. See, e.g., the CAS-200 system (Becton, Dickinson & Co.).

Antibodies for use in the present invention include any antibody, whether natural or synthetic, full length or a fragment thereof, monoclonal or polyclonal, that binds sufficiently strongly and specifically to the biomarker that is to be detected. An antibody can have a $K_d$ of at most about $10^{-6}$M, $10^{-7}$M, $10^{-8}$M, $10^{-9}$M, $10^{-10}$M, $10^{-11}$M and $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant.

Antibodies and derivatives thereof that can be used encompasses polyclonal or monoclonal antibodies, chimeric, human, humanized, primatized (CDR-grafted), veneered or single-chain antibodies, phase produced antibodies (e.g., from phage display libraries), as well as functional binding fragments, of antibodies. For example, antibody fragments capable of binding to a biomarker, or portions thereof, including, but not limited to Fv, Fab, Fab' and F(ab')$_2$ fragments can be used. Such fragments can be produced by enzymatic cleavage or by recombinant techniques. For example, and not by way of limitation, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0125023 B1; Boss et al., U.S. Pat. No. 4,816,397; Boss et al., European Patent No. 0,120,694 B1; Neuberger, M. S. et al., WO 86/01533; Neuberger et al., European Patent No. 0,194,276 B1; Winter, U.S. Pat. No. 5,225,539; Winter, European Patent No. 0,239,400 B1; Queen et al., European Patent No. 0451216 B1; and Padlan et al., EP 0519596 A1. See also, Newman et al., BioTechnology, 10: 1455-1460 (1992), regarding primatized antibody, and Ladner et al., U.S. Pat. No. 4,946,778 and Bird et al., Science, 242: 423-426 (1988)) regarding single-chain antibodies.

In certain embodiments, Enigma is detected using an Enigma-specific antibody sold by Santa Cruz, Cat. No. SC-98370 (H110; "the '370 Ab"), a fragment thereof, or an antibody that competitively inhibits binding of the '370 Ab to Enigma.

In certain embodiments, agents that specifically bind to a polypeptide other than antibodies can be used, such as peptides. Peptides that specifically bind can be identified by any means known in the art, e.g., peptide phage display libraries. Generally, an agent that is capable of detecting a biomarker polypeptide, such that the presence of a biomarker is detected and/or quantitated, can be used. As defined herein, an "agent" refers to a substance that is capable of identifying or detecting a biomarker in a biological sample (e.g., identifies or detects the mRNA of a biomarker, the DNA of a biomarker or the protein of a biomarker). In certain embodiments, the agent is a labeled or a labelable peptide, which specifically binds to a biomarker polypeptide.

In certain embodiments, where the amount of CDH18 mRNA is to be evaluated, one or more nucleic acid probes or primers may be used using quantitative Northern blot and/or polymerase chain reaction technology or other methods known in the art.

5.2 CDK4 Inhibitors

Non-limiting examples of CDK4 inhibitors include compounds that inhibit and/or reduce the kinase activity of CDK4, for example human CDK4. Non-limiting examples of CDK4 inhibitors include ATP-competitive inhibitors of CDK4. In particular non-limiting embodiments, the CDK4 inhibitor is derived from pyridopyrimidine, pyrrolopyrimidine or indolocarbazole compounds. Further non-limiting examples of CDK4 inhibitors include Palbociclib free base and Palbociclib salts such as Palbociclib Isethionate, LEE011 ("ribociclib"; CAS Number 1211441-98-3), LY2835219 ("abemaciclib"; CAS Number 1231930-82-7), PD0332991, P1446A-05, G1T28 ("trilaciclib") and Flavopiridol Hydrochloride. Additional CDK4 inhibitors are disclosed in U.S. Pat. Nos. 6,630,464 and 6,818,663, and U.S. Patent Application Nos. 2012/0244110, 2012/0207763 and 2011/0152244.

Further non-limiting examples of CDK4 inhibitors include antisense oligonucleotides, shRNA molecules and siRNA molecules that specifically inhibit the expression or activity of CDK4. One non-limiting example of a CDK4 inhibitor comprises an antisense, shRNA, or siRNA nucleic acid sequence homologous to at least a portion of a CDK4 nucleic acid sequence, wherein the homology of the portion relative to the CDK4 sequence is at least about 75 or at least about 80 or at least about 85 or at least about 90 or at least about 95 or at least about 98 percent, where percent homology can be determined by, for example, BLAST or FASTA software. In certain non-limiting embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. In certain embodiments, the CDK4 inhibitor is a shRNA comprising the nucleic acid sequence GAGATTACTTTGCTGCCTTAA (SEQ ID NO: 3). shRNA Antisense, shRNA or siRNA molecules may comprise DNA or atypical or non-naturally occurring residues, for example, but not limited to, phosphorothioate residues.

5.3 Enigma Inhibitors

Non-limiting examples of Enigma inhibitors include compounds that inhibit and/or reduce the activity of Enigma.

Further non-limiting examples of Enigma inhibitors include antisense oligonucleotides, shRNA molecules and siRNA molecules that specifically inhibit the expression or activity of Enigma. One non-limiting example of an Enigma inhibitor comprises an antisense, shRNA, or siRNA nucleic acid sequence homologous to at least a portion of an Enigma nucleic acid sequence, wherein the homology of the portion relative to the Enigma sequence is at least about 75 or at least about 80 or at least about 85 or at least about 90 or at least about 95 or at least about 98 percent, where percent homology can be determined by, for example, BLAST or FASTA software. In certain non-limiting embodiments, the complementary portion may constitute at least 10 nucleotides or at least 15 nucleotides or at least 20 nucleotides or at least 25 nucleotides or at least 30 nucleotides and the antisense nucleic acid, shRNA or siRNA molecules may be up to 15 or up to 20 or up to 25 or up to 30 or up to 35 or up to 40 or up to 45 or up to 50 or up to 75 or up to 100 nucleotides in length. shRNA Antisense, shRNA or siRNA molecules may comprise DNA or atypical or non-naturally occurring residues, for example, but not limited to, phosphorothioate residues.

5.4 Cancer Targets

Non-limiting examples of cancers that may be subject to the present invention include liposarcoma, glioma (or glioblastoma), osteosarcomas, melanoma, oligodendroglioma, astrocytoma, neuroblastoma, pancreatic neuroendocrine tumors, prostate cancer, non-small cell lung cancer and breast cancer.

5.5 Methods of Use

In certain non-limiting embodiments, the present invention provides for a method of determining whether an anti-cancer effect is likely to be produced in a cancer by a CDK4 inhibitor. In certain embodiments, a method of the present invention comprises detecting a biomarker, e.g., an Enigma and/or a CDH18 biomarker, in a cancer or a sample of the cancer, where if the biomarker is localized to foci in the cancer prior to and/or following CDK4 inhibition, it is more likely that the CDK4 inhibitor would have an anti-cancer effect on the cancer relative to a cancer in which the biomarker is not localized to foci. In certain non-limiting embodiments the biomarker is localized to foci prior to CDK4 inhibition. In certain non-limiting embodiments the biomarker is localized to foci following CDK4 inhibition.

In certain non-limiting embodiments, a method of the present invention comprises detecting a biomarker, e.g., an Enigma and/or a cadherin biomarker, in a cancer or a sample of the cancer, where if the biomarker is localized to foci in the cancer prior to and/or following CDK4 inhibition, it is more likely that the CDK4 inhibitor would have an anti-cancer effect on the cancer relative to a cancer in which the biomarker is not localized to foci. In certain non-limiting embodiments the biomarker is localized to foci prior to CDK4 inhibition. In certain non-limiting embodiments the biomarker is localized to foci following CDK4 inhibition.

Enigma and CDH18 biomarkers are described in the sections above. CDK4 inhibitors are described above. Enigma inhibitors are described above. Cancers suitable for treatment are described above. Methods for detecting and determining the localization of an Enigma and/or a CDH18 biomarker are set forth above.

In certain embodiments, the localization pattern of the biomarker may be appreciated by comparing the localization of the biomarker in the cancer to a reference sample. For example, and not by way of limitation, the reference sample can be a responsive cell. A "responsive cell" also referred to as a "responder cell" is a cancer cell which, when treated with an effective amount of a CDK4 inhibitor, increases expression of one or more markers of the senescent phenotype, including, but not limited to SA-β-gal, senescence-associated heterochromatin foci and elaboration of the senescence-associated secretory program and/or increases the number of ATRX foci in the nucleus and/or exhibits a decrease in MDM2 protein, relative to the level without treatment with the CDK4 inhibitor.

In certain embodiments, the reference sample can be a non-responsive cell. A "non-responsive cell" also referred to as a "non-responder cell" is a cancer cell, which is not a responder cell. In certain non-limiting embodiments, a non-responder cell, when treated with an amount of a CDK4 inhibitor effective in inducing senescence in responder cells, does not increase expression of at least one marker, or at least two markers, or at least three markers, of the senescent phenotype selected from the group consisting of SA-β-gal, senescence-associated heterochromatin foci and elaboration of the senescence-associated secretory program and/or does not increase the number of ATRX foci in the nucleus and/or exhibits stable or increased levels of MDM2 protein, relative to the level without treatment with the CDK4 inhibitor.

A subject may be human or a non-human subject. Non-limiting examples of non-human subjects include non-human primates, dogs, cats, mice, rats, guinea pigs, rabbits, pigs, fowl, horses, cows, goats, sheep, cetaceans, etc.

An anti-cancer effect means one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate, a reduction in tumor metastasis, an increase in the proportion of senescent cancer cells, an increase in the duration of time to relapse, an increase in survival and/or an increased survival without tumor progression.

In certain non-limiting embodiments, a sample includes, but is not limited to, a clinical sample, cells in culture, cell supernatants, cell lysates, serum, blood plasma, biological fluid (e.g., lymphatic fluid) and tissue samples. The source of the sample may be solid tissue (e.g., from a fresh, frozen, and/or preserved organ, tissue sample, biopsy or aspirate), blood or any blood constituents, bodily fluids (such as, e.g., urine, lymph, cerebral spinal fluid, amniotic fluid, peritoneal fluid or interstitial fluid), or cells from the individual, including circulating tumor cells. In certain non-limiting embodiments, the sample is obtained from a tumor.

In certain non-limiting embodiments, the present invention provides for a method for determining whether an anti-cancer effect is likely to be produced in a cancer by a CDK4 inhibitor, comprising, obtaining a sample of the cancer before treatment with a CDK4 inhibitor, and detecting, in the sample, a biomarker, e.g., an Enigma and/or a CDH18 biomarker, where if the biomarker is localized to foci in the sample, it is more likely that a CDK4 inhibitor would have an anti-cancer effect on the cancer relative to a cancer in which the biomarker(s) is/are not localized to foci. For example, and not by way of limitation, the biomarker can be aCDH18 biomarker. In certain embodiments, the biomarker can be a CDH18 biomarker detected by the '6M1 Ab, or fragment thereof, or an antibody that competitively inhibits binding of the '6M1 Ab to CDH18. In certain embodiments, the biomarker can be an Enigma biomarker. In certain embodiments, the biomarkers can be Enigma and CDH18 biomarkers. In certain embodiments, the presence of any of the foregoing biomarkers or combinations of biomarkers in foci can be tested, and the level of CDH18 protein or mRNA may be compared to a reference responder or non-responder cell (where higher levels are found in responder than non-responder cells).

In certain non-limiting embodiments, the present invention provides for a method for determining whether an anti-cancer effect is likely to be produced in a cancer by a CDK4 inhibitor, comprising, obtaining a sample of the cancer before treatment with a CDK4 inhibitor, and detecting, in the sample, a combination of an Enigma biomarker, and a CDH18 biomarker, where if the biomarkers colocalize to foci in the sample, it is more likely that a CDK4 inhibitor would have an anti-cancer effect on the cancer relative to a cancer in which the CDH18 and Enigma are not colocalized to foci.

In certain non-limiting embodiments, the present invention provides for a method for producing an anti-cancer effect by a CDK4 inhibitor in a subject, comprising, obtaining a sample of the cancer before treatment of the subject with a CDK4 inhibitor, and detecting, in one or more cancer cells from the sample, a biomarker, e.g., an Enigma and/or a CDH18 biomarker, where if the biomarker(s) is/are localized to foci in the one or more cancer cells from the sample, then initiating treatment of the subject with a therapeutically effective amount of the CDK4 inhibitor. In certain embodiments, the method comprises detecting at least one CDH18 biomarker and at least one Enigma biomarker in one or more cancer cells, where if the CDH18 and the Enigma biomarkers colocalize to foci in the one or more cancer cells, then treatment of the subject with a therapeutically effective amount of the CDK4 inhibitor is initiated. In certain embodiments, the presence of the foregoing combination of biomarkers in foci can be tested, and the level of CDH18 protein or mRNA may be compared to a reference responder or non-responder cell (where higher levels are found in responder than non-responder cells), and this result can be considered in determining whether to administer CDK4 inhibitor therapy or not. In certain non-limiting embodiments, where the Enigma and/or CDH18 biomarkers do not localize to foci and/or do not colocalize to foci in the one or more cancer cells before treatment with a CDK4 inhibitor, the subject from whom the cancer cells are derived is to be treated with another modality, for example, an alternative chemotherapeutic agent, biologic anti-cancer agent, or radiation therapy. In certain non-limiting embodiments, where the Enigma and/or CDH18 biomarkers do not localize or do not colocalize to foci in the one or more cancer cells before treatment with a CDK4 inhibitor, the subject from whom the cancer cells are derived is to be treated with a CDK4 inhibitor and an Enigma inhibitor.

A therapeutically effective amount is an amount that is able to achieve one or more of an anti-cancer effect, prolongation of survival and/or prolongation of period until relapse.

In certain non-limiting embodiments, the present invention provides for a method for producing an anti-cancer effect by a CDK4 inhibitor, comprising, obtaining a sample of the cancer after treatment with a CDK4 inhibitor, and detecting, in one or more cancer cells from the sample, a biomarker, e.g., an Enigma and/or a CDH18 biomarker, where if the biomarker is localized to foci in the one or more cancer cells from the sample, then continuing or resuming treatment of the subject with a therapeutically effective amount of a CDK4 inhibitor. In certain embodiments, the method comprises detecting at least one CDH18 biomarker and at least one Enigma biomarker, where if the CDH18 and the Enigma biomarkers colocalize to foci in the one or more cancer cells from the sample, then treatment of the subject with a therapeutically effective amount of the CDK4 inhibitor is continued or resumed. In certain embodiments, the presence of the foregoing combination of biomarkers in foci can be tested, and the level of CDH18 protein or mRNA may be compared to a reference responder or non-responder cell (where higher levels are found in responder than non-responder cells), and this result be considered in determining whether to administer CDK4 inhibitor therapy or not. In certain non-limiting embodiments, where the Enigma and/or CDH18 biomarkers do not localize to foci and/or do not colocalize to foci in the one or more cancer cells after treatment with a CDK4 inhibitor, the subject from whom the cancer cells are derived is to be treated with another modality, for example, an alternative chemotherapeutic agent, biologic anticancer agent, or radiation therapy. In certain non-limiting embodiments, where the Enigma and/or CDH18 biomarkers do not localize or do not colocalize to foci in the one or more cancer cells after treatment with a CDK4 inhibitor, the subject from whom the cancer cells are derived is to be treated with a CDK4 inhibitor and an Enigma inhibitor.

In certain non-limiting embodiments, the present invention provides for a method for treating a subject having a cancer, comprising, obtaining a sample of the cancer after treatment with a CDK4 inhibitor, and detecting, in the sample, a biomarker, e.g., an Enigma biomarker and/or a CDH18 biomarker, where if the biomarker(s) is/are localized to foci following treatment with a CDK4 inhibitor as compared to a reference sample, then continuing or resuming treatment of the subject with a therapeutically effective amount of a CDK4 inhibitor. In certain embodiments, the method comprises detecting at least one CDH18 biomarker and at least one Enigma biomarker, where if the CDH18 and the Enigma biomarkers colocalize to foci in the one or more cancer cells from the sample as compared to a reference sample, then treatment of the subject with a therapeutically effective amount of the CDK4 inhibitor is continued or resumed. For example, and not by way of limitation, if the biomarker localizes to foci and/or if the biomarkers colocalize as compared to the reference sample that is a responsive cell, than treatment of the subject with a therapeutically effective amount of a CDK4 inhibitor is continued or resumed. In certain embodiments, if the biomarker does not localize to foci and/or if the biomarkers do not colocalize as compared to the reference sample that is a responsive cell, than treatment of the subject with a therapeutically effective amount of a CDK4 inhibitor is not continued or resumed.

Any of the foregoing methods may further comprise a step of detecting one or more markers for senescence in a sample following treatment with a CDK4 inhibitor. For example, and not by way of limitation, methods of the present disclosure can further comprise detecting SA-β-gal, senescence-associated heterochromatin foci and the elaboration of the senescence-associated secretory program and/or detection of ATRX foci. In certain embodiments, any of the foregoing methods may further comprise determining the level of MDM2, e.g., MDM2 protein, in a sample.

In certain non-limiting embodiments, the invention provides for a method for determining whether an anti-cancer effect is likely to be produced in a cancer by n CDK4 inhibitor, comprising determining the relative level of CDH18 expression in a cell of the cancer relative to the level of CDH18 expression in a reference non-responder cell, where if the level of expression in the cancer cell is greater than the level of expression in the reference cell, it is more likely that a CDK4 inhibitor would have an anti-cancer effect on the cancer.

5.6 Kits

In non-limiting embodiments, the present invention provides for a kit for determining whether an anti-cancer effect is likely to be produced in a cancer by a CDK4 inhibitor, comprising a means for detecting the localization of a biomarker, e.g., an Enigma and/or a CDH18 biomarker. Enigma and CDH18 biomarkers and methods for determining the localization of the biomarkers are described in the sections above.

Types of kits include, but are not limited to, biomarker-specific antibodies and beads, which can further contain one or more probes, agents, antibodies or other detection reagents for detecting one or more biomarkers of the present invention.

In non-limiting embodiments, the present invention provides for a kit for determining whether the anti-cancer effect is likely to be produced in a cancer by a CDK4 inhibitor, comprising a means for detecting, e.g., determining the localization of, a biomarker.

In non-limiting embodiments, a kit may comprise at least one antibody for immunodetection of the biomarker(s) to be identified. Antibodies, both polyclonal and monoclonal, including molecules comprising an antibody variable region, specific for a CDH18 or an Enigma biomarker, may be prepared using conventional immunization techniques, as will be generally known to those of skill in the art. The immunodetection reagents of the kit may include detectable labels that are associated with, or linked to, the given antibody or antigen itself. Such detectable labels include, for example, chemiluminescent or fluorescent molecules (rhodamine, fluorescein, green fluorescent protein, luciferase, Cy3, Cy5, or ROX), radiolabels ($^3$H, $^{35}$S, $^{32}$P, $^{14}$C and $^{131}$I) or enzymes (alkaline phosphatase, horseradish peroxidase). Alternatively, a detectable moiety may be comprised in a secondary antibody or antibody fragment, which selectively binds to the first antibody or antibody fragment (where said first antibody or antibody fragment specifically recognizes CDH18 or Enigma).

In one specific non-limiting embodiment, a kit may comprise an agent, probe or antibody suitable for detecting an Enigma biomarker.

In one specific non-limiting embodiment, a kit may comprise an agent, probe or antibody suitable for detecting a CDH18 biomarker.

In certain embodiments, a kit of the present invention comprises a first antibody that is specific to an Enigma biomarker and a second antibody that is specific for a CDH18 biomarker. For example, the antibodies may recognize human biomarkers. For example, the kit may contain no more than five, no more than ten, or no more than twenty species of antibodies (i.e., types of antibodies directed toward different targets).

In certain embodiments, a kit of the present invention comprises a first antibody, or antibody fragment, that is specific to an Enigma biomarker, and a second antibody, or antibody fragment, that is specific for a CDH18 biomarker. For example, the antibodies may recognize human biomarkers. For example, the kit may contain no more than five, no more than ten, or no more than twenty species of antibodies (i.e., types of antibodies directed toward different targets).

In certain non-limiting embodiments, a kit may further contain means for detecting a marker for senescence. For example, in certain non-limiting embodiments, the kit may further comprise an antibody suitable for detecting senescence-associated heterochromatic foci (SAHF), e.g., an antibody specific for HP1γ. In certain non-limiting embodiments, the kit may comprise an antibody suitable for detecting senescence-associated β-galactosidase.

In certain non-limiting embodiments, a biomarker detection kit may comprise one or more detection reagents and other components (e.g., a buffer, enzymes such as alkaline phosphatase, antibodies, and the like) necessary to carry out an assay or reaction to determine the localization of a biomarker.

A kit may further include instructions for using the kit to determine and/or evaluate the localization of a CDH18 and/or an Enigma biomarker. Specifically, in certain embodiments, the instructions describes that the localization of an Enigma and/or a CDH18 biomarker to foci, before and/or after treatment with a CDK4 inhibitor, set forth herein, is indicative of an increased possibility of an anti-cancer effect in a cancer by a CDK4 inhibitor.

A kit may further comprise a positive and/or a negative control, for example, a responder and/or a non-responder cell sample or facsimile thereof.

In certain embodiments, a kit may comprise means for determining the relative amount of CDH18 expression, for example, an antibody to evaluate the relative amount of CDH18 protein and/or a nucleic acid probe, primer, or primer pair to detect the amount of CDH18 mRNA, optionally together with one or more positive control (e.g. a sample containing a reference amount of protein or RNA).

6. EXAMPLE 1: ENIGMA CO-LOCALIZES WITH CDH18 IN RESPONDER Cells

Previous studies have shown that senescence of cancer cells is associated with and driven by a reduction in the proteins levels of MDM2 (Kovatcheva et al. Oncotarget, 6(10):8226-8243 (2015)). In addition, it has been previously shown that knockdown of HAUSP was sufficient to reduce MDM2 protein levels and drive senescence in responder cells versus non-responder cells (Kovatcheva et al. (2015), supra).

Figure 1:
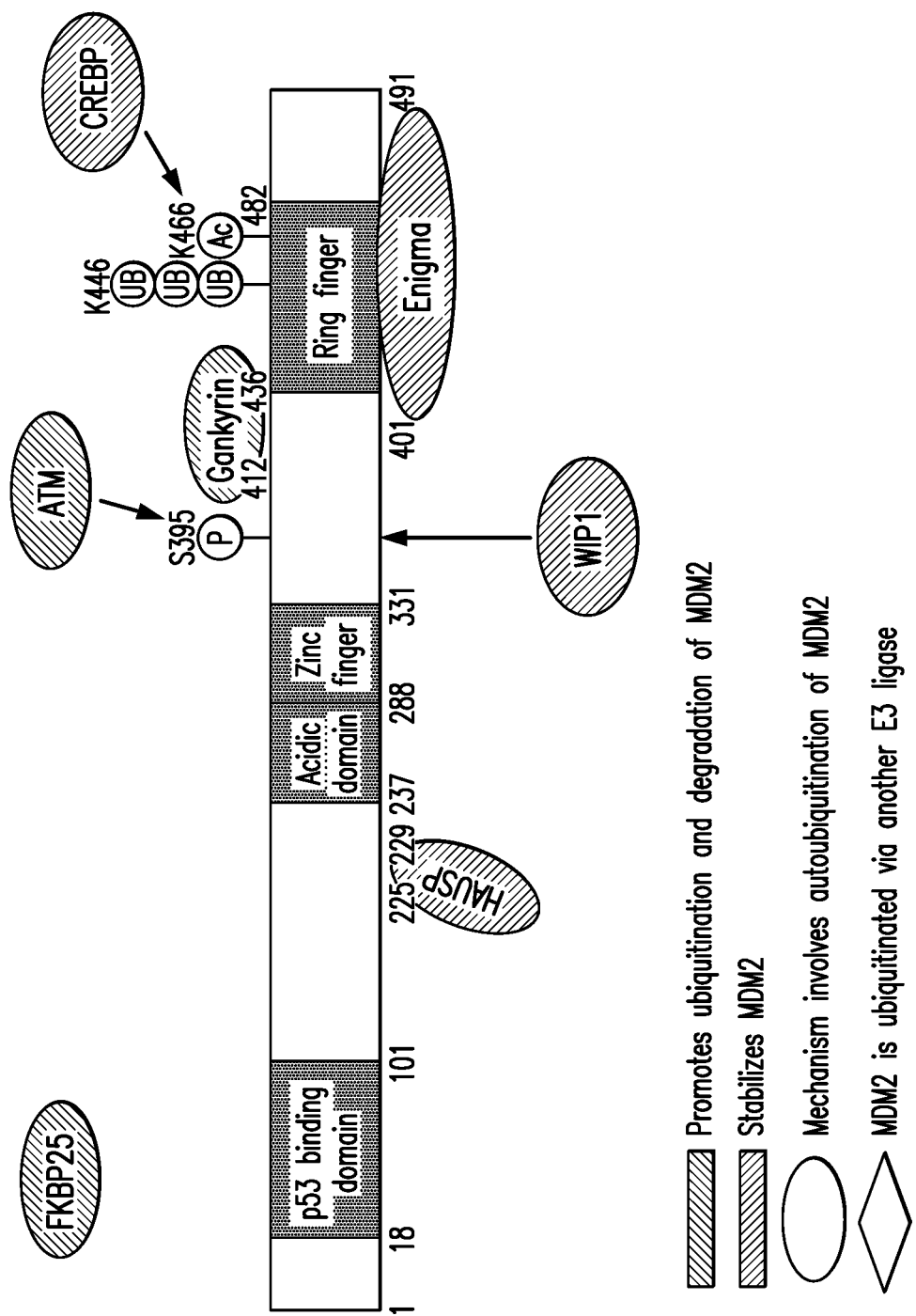
FIG. 1 depicts a schematic showing the structural domains of MDM2.
Figure 2:
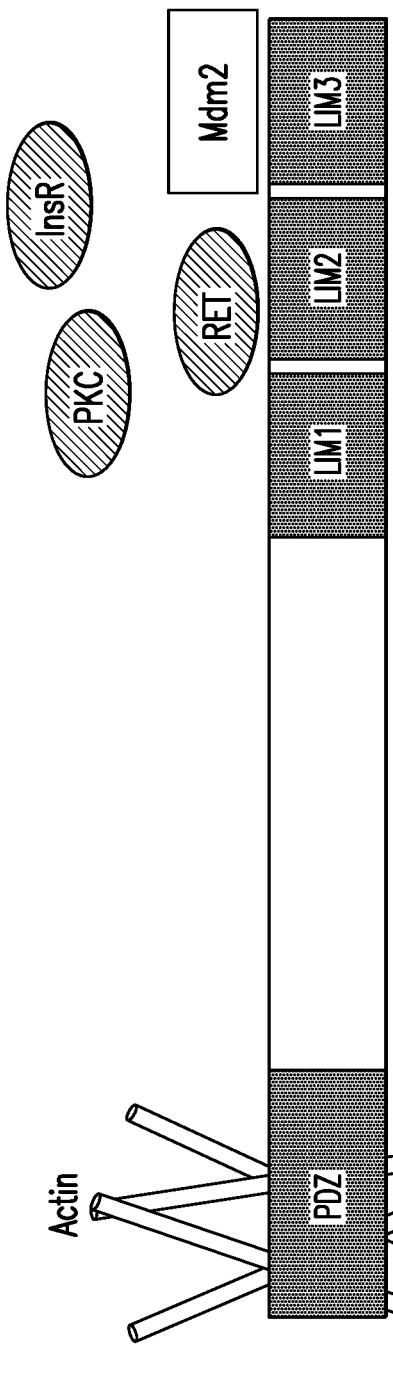
FIG. 2 depicts a schematic showing the structural domains of Enigma.

To determine the mechanism by which senescence is blocked in non-responder cells in response to CDK4 inhibition or knockdown of HAUSP, analysis of potential proteins that can interact with MDM2 was performed (FIG. 1). As shown in FIG. 2, Enigma, which is also known as PDZ And LIM Domain 7 (PDLIM7), can interact with 5 proteins (FIG. 2) (Durick et al. Mol. and Cell. Bio. 18(4):2298-2308 (1998); Kuroda et al., J. Biol. Chem. 271:31029-31032 (1996); Wu et al., J. Biol. Chem. 271:15934-15941 (1996); and Jung et al. J. of Clinical Investigation 120(12):4493-4506 (2010)). It was previously shown that binding of MDM2 and Enigma blocks MDM2 autoubiquitination (Jung et al. (2010)).

To determine if Enigma plays a role in the reduction of MDM2 levels, Enigma expression levels were reduced using two independent short hairpins in the non-responder cell line LS8107. The short hairpins used are as follows: TRCN0000161061: GCGAGACTATGAGAAGATGTT (SEQ ID NO: 4); and TRCN0000166638 ("EN638"): CGTCTGTGCGATATGTCAGAT (SEQ ID NO: 5). As shown in FIG. 3A-D, LS8107 cells do not reduce their MDM2 protein levels and do not undergo senescence upon treatment with the CDK4 inhibitor PD0332991 as determined by the number of SA-β-gal positive cells. However, when Enigma is knocked down, treatment with PD0332991 resulted in a reduction in MDM2 protein levels and the cells entered senescence (FIG. 3D).

To determine if Enigma affects MDM2 protein levels post-translationally, the turnover of MDM2 was analyzed. As shown in FIG. 4B, knockdown of Enigma affected MDM2 in a post-translational manner, as the addition of PD0332991 increased the turnover of MDM2, which typically occurs in responder cell lines. To determine whether HAUSP and Enigma are the important regulators of MDM2 protein levels in response to treatment with a CDK4 inhibitor, concomitant knockdown of HAUSP and Enigma was performed. As shown in FIG. 5A-C, in LS8107 cells, treatment with PD0332991 alone, knockdown of HAUSP expression levels alone and knockdown of Enigma expression levels alone were insufficient to induce senescence. However, concomitant knockdown of HAUSP and Enigma in the absence of PD0332991 treatment was sufficient to induce senescence (FIG. 5A-B), as indicated by the percent SA-β-Gal and the average number of ATRX+ foci).

To determine if Enigma interacts with MDM2, co-immunoprecipitation experiments were performed. Enigma tagged with GFP was expressed in non-responder and responder cells, and co-immunoprecipitation of MDM2 and Enigma-GFP was performed. As shown in FIG. 7A, Enigma does not associate with MDM2 in responder cells (e.g., LS8817 cells). However, an interaction between MDM2 and Enigma was observed in non-responder LS8107 cells (FIG. 7A). Additionally, this is not a liposarcoma specific effect as this interaction can be detected in a cycling and PD0332991-arrested non-small cell lung carcinoma cell line that undergoes quiescence (FIG. 7B). Further, this interaction difference cannot just be explained by lack of protein, as there are no differences in protein levels of Enigma in these cell lines (FIG. 7C).

To determine if the difference in interaction is due to a change in localization between responder and non-responder cells, immunofluorescence was performed. As shown in FIG. 8, Enigma was observed to localize to foci in responder cells; whereas, Enigma was observed to be diffuse throughout the cell in non-responder cells. To further characterize these foci, immunofluorescence was performed with a number of cytoskeletal proteins including Actin, γ-tubulin. Vimentin, and cadherin (FIG. 9). No significant differences were observed in the localization pattern of Actin, γ-tubulin. Vimentin proteins between non-responder and responder cells. However, a difference in cadherin localization between responders and non-responder cells was detected by a pan-cadherin antibody sold by BD Biosciences, incorrectly marketed as E-cadherin specific, Cat. No. 610181 ("the '181Ab"). This antibody cross-reacts with CDH18 as this pattern was later confirmed using a CDH18-specific antibody and appropriate knockdown of the target. The cadherin localized to foci in responders and was diffuse in non-responders (FIG. 9). The differences in cadherin localization is not a liposarcoma-specific phenomenon, as a glioma, breast and NSCLC cell line that undergo senescence also have these foci; whereas, a non-responder NSCLC cell line does not (FIG. 10). To further determine the relationship between cadherin and Enigma, immunofluorescence was performed to determine if cadherin and Enigma colocalized in responder cells. As shown in FIG. 11, cadherin and Enigma colocalize to the foci in responder cells. Without being limited to a particular theory, colocalization of cadherin and Enigma by immunofluorescence suggests that these proteins are present within 400-600 nm of one another.

To determine how close cadherin and Enigma reside within responder cells, a proximity ligation assay was performed. In the proximity ligation assay, the same primary antibodies were incubated overnight with the sample. However, in place of using secondary antibodies tagged with fluorophores, secondary antibodies that were conjugated to oligonucleotide probes were used. If the two proteins interact within 40 nm of one another the probes will ligate and amplify, and the localization will be identified by fluorescently-labeled oligonucleotide probes. As shown in FIG. 12, cadherin and Enigma colocalized in responder cells but not in non-responder cells as determined by the proximity ligation assay. These data suggest that the proteins may interact with one another and that the colocalization of these two proteins is a good indicator that the cell will likely be responsive to CDK4 inhibition.

To further confirm that the presence of cadherin and Enigma localize to foci in responder cells upon senescence, responder cells were placed under conditions where the cells undergo quiescence and fail to undergo senescence, e.g., to become a non-responsive cell. Responder cells were placed under serum starvation conditions (0.5% FBS), which causes the cells to exit the cell cycle but MDM2 is not reduced and senescence does not occur (FIG. 13A-D). As shown in FIG. 13C-D, under serum starvation conditions, a loss of the foci was observed and an interaction between Enigma and MDM2 was detected. Without being limited to a particular theory, cadherin present within the foci may sequester Enigma away from MDM2 so that when PD0332991 causes the dissociation of MDM2 and HAUSP, MDM2 is degraded (FIG. 14). In contrast, in non-responder cells, which do not have cadherin foci, Enigma remains bound to MDM2 even upon the dissociation of HAUSP, thereby preventing MDM2 degradation (FIG. 14).

To determine if the colocalization of cadherin and Enigma can be used in the clinical setting, the proximity ligation assay was performed on formalin fixed paraffin embedded samples as human biopsies of cancers are often stored as formalin fixed paraffin embedded samples. As shown in FIG. 15A-B, the use of the proximity ligation assay in responder and non-responder cells showed a difference in the colocalization of Enigma and cadherin between the two cell types. To determine if the proximity ligation assay can be used on patient samples as a diagnostic tool, a number of liposarcoma samples from patients that were formalin fixed paraffin embedded were analyzed (FIG. 16). The patient samples were stained with DAPI to identify the large nuclei of tumor cells. The outlines of the large nuclei were superimposed on the proximity ligation analysis channel to identify the tumor cells that had colocalization of cadherin and Enigma and those that did not. FIG. 16 shows a patient sample, S09 38706, that exhibits colocalization of cadherin and Enigma (solid arrows) and would be considered responsive; whereas, in patient sample S12 7834, the majority of tumor cells did not exhibit colocalization of cadherin and Enigma (open arrows) and would be considered non-responsive.

As shown by the schematic in FIG. 17, it is believed that upon treatment with the CDK4 inhibitor, HAUSP disassociates from MDM2, which can then undergo autoubiquitination in responder cells and induce senescence. In responder cells, Enigma colocalizes with cadherin and does not block autoubiquitination of MDM2. In non-responder cells, Enigma interacts with MDM2 to block autoubiquitination and prevent cells from entering senescence when treated with a CDK4 inhibitor.

FIG. 18 shows knockdown of various cadherins (CDH1, CDH2, CDH3, CDH4, CDH5, CDH11, CDH12, CDH15, CDH16 and CDH18) by shRNA and its effects on the reduction of foci.

Figure 19A:
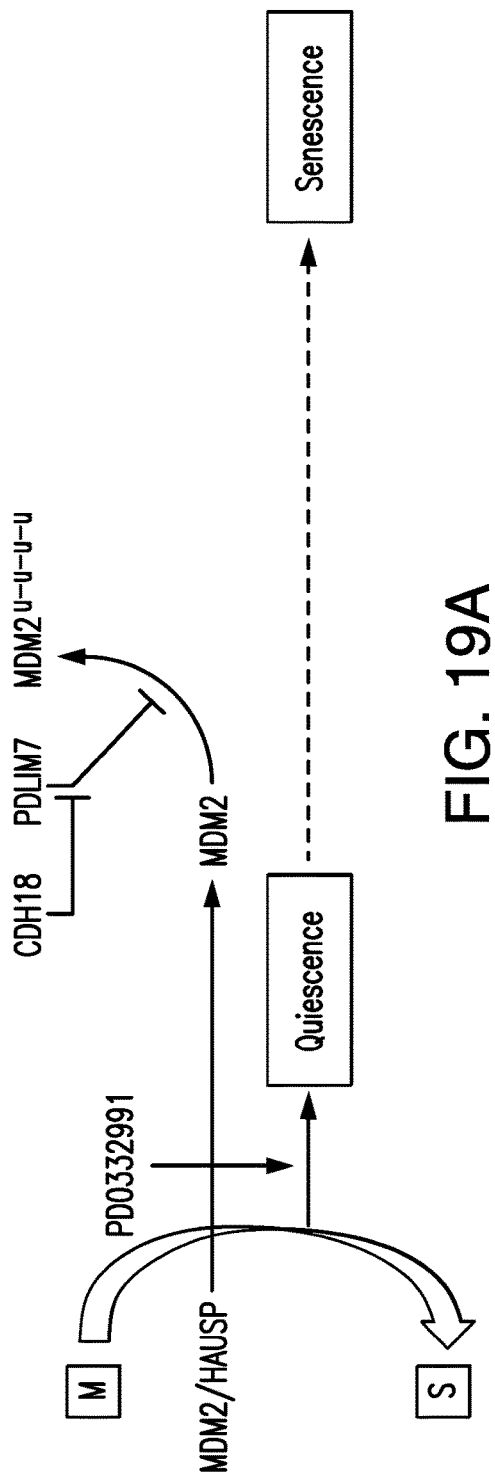
Figure 19B:
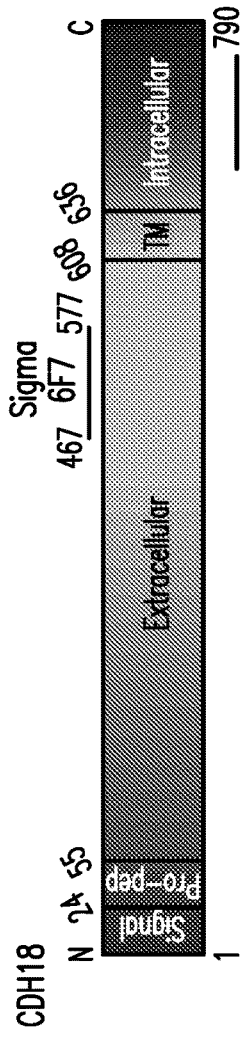
Figure 19C:
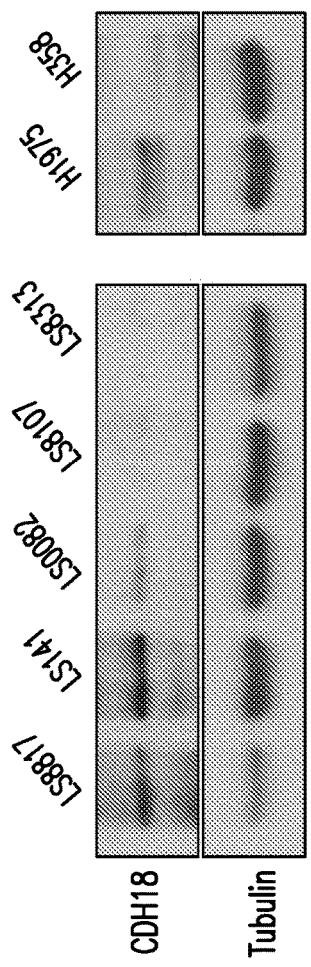
Figure 19D:
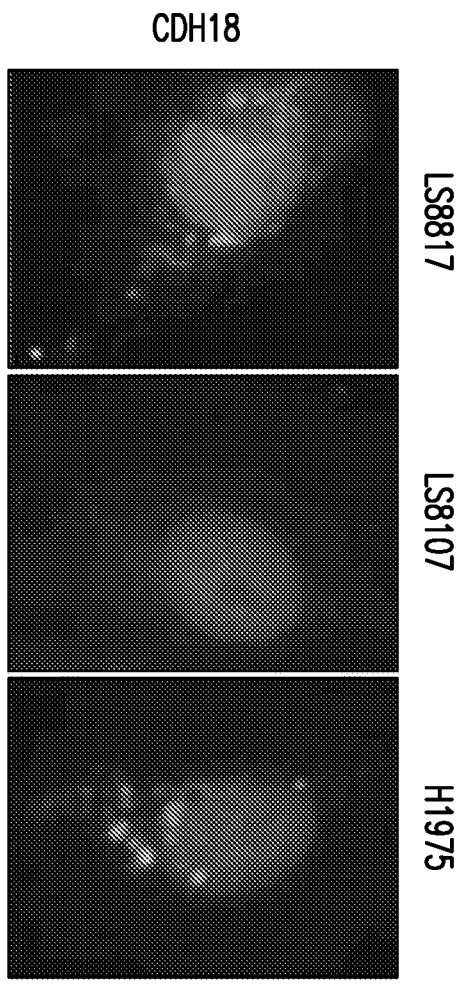

It has further been determined that CDH18 occurs in foci and is expressed at higher levels in responder compared to non-responder cell lines. In particular, it was found that mRNA expression of CDH18 was lower in two out of the three non-responder cell lines tested. In the third non-responder cell line, the level of CDH18 was similar to the level in responder cells, but no interaction with PDLIM7/ENIGMA was observed. CDH18 may inhibit the association between Enigma (PDLIM7) and the ubiquination of MDM2 (FIG. 19A). Higher levels of CDH18 expression were observed in responder cell lines LS8817, LS141, and H1975 relative to non-responder cell lines LS8107, LS8313, and H358 (FIG. 19C-D), a difference that was also observed at the mRNA level (FIG. 19E).

Various references and Sequence Accession Numbers are cited herein, the contents of which are hereby incorporated by reference in their entireties.

What is claimed is:

1. A method for selecting cancer patients for treatment with a CDK4 inhibitor, comprising
   (a) detecting CDH18 protein expression pattern within one or more cancer cells present in samples obtained from cancer patients;
   (b) selecting cancer patients in which CDH18 protein is localized to foci within the one or more cancer cells; and
   (c) administering an effective amount of a CDK4 inhibitor to the cancer patients of step (b), wherein the cancer is selected from the group consisting of liposarcoma, glioma, non-small cell lung cancer, and breast cancer.

2. The method of claim 1, wherein CDH18 is detected by immunofluorescence.

3. The method of claim 1, wherein the cancer is a liposarcoma.

4. The method of claim 1, wherein the cancer is a glioma.

5. The method of claim 1, wherein the cancer is a non-small cell lung cancer.

6. The method of claim 1, wherein the cancer is a breast cancer.

7. A method for treating cancer in cancer patients that have received CDK4 inhibitor therapy, comprising (a) detecting CDH18 protein expression pattern within one or more cancer cells present in samples obtained from the cancer patients that have received CDK4 inhibitor therapy;
(b) selecting cancer patients in which CDH18 protein is localized to foci within the one or more cancer cells; and
(c) administering an effective amount of a CDK4 inhibitor to the cancer patients of step (b), wherein the cancer is selected from the group consisting of liposarcoma, glioma, non-small cell lung cancer, and breast cancer.

8. The method of claim 7, wherein the cancer is a liposarcoma.

9. The method of claim 7, wherein the cancer is a glioma.

10. The method of claim 7, wherein the cancer is a non-small cell lung cancer.

11. The method of claim 7, wherein the cancer is a breast cancer.

12. The method of claim 1, wherein the CDK4 inhibitor is palbociclib, ribociclib, abemaciclib, PD0332991, P1446A-05, trilaciclib, flavopiridol hydrochloride, a CDK4 antisense oligonucleotide, a CDK4 shRNA, or a CDK4 siRNA.

13. The method of claim 7, wherein the CDK4 inhibitor is palbociclib, ribociclib, abemaciclib, PD0332991, P1446A-05, trilaciclib, flavopiridol hydrochloride, a CDK4 antisense oligonucleotide, a CDK4 shRNA, or a CDK4 siRNA.

* * * * *